US012643861B2

(12) United States Patent (10) Patent No.: US 12,643,861 B2
He et al. (45) Date of Patent: Jun. 2, 2026

(54) CRYSTALLINE FORM OF FLUVATINIB OR FLUVATINIB METHANESULFONATE AND PREPARATION METHOD THEREFOR

(71) Applicants: CHONGQING PHARMACEUTICAL RESEARCH INSTITUTE CO., LTD, Chongqing (CN); YAOPHARMA CO., LTD., Chongqing (CN)

(72) Inventors: Shuai He, Chongqing (CN); Yang Zhang, Jiangsu (CN); Qiang Liu, Chongqing (CN); Zhengxia Chen, Jiangsu (CN); Meibi Dai, Jiangsu (CN); Bin Fan, Chongqing (CN); Peiyu Xie, Chongqing (CN)

(73) Assignees: CHONGQING PHARMACEUTICAL RESEARCH INSTITUTE CO., LTD, Chongqing (CN); YAOPHARMA CO., LTD., Chongqing (CN)

( * ) Notice: Subject to any disclaimer, the term of this patent is extended or adjusted under 35 U.S.C. 154(b) by 747 days.

(21) Appl. No.: 17/793,406

(22) PCT Filed: Mar. 16, 2021

(86) PCT No.: PCT/CN2021/081023
§ 371 (c)(1),
(2) Date: Jul. 17, 2022

(87) PCT Pub. No.: WO2021/143954
PCT Pub. Date: Jul. 22, 2021

(65) Prior Publication Data
US 2023/0106064 A1 Apr. 6, 2023

(30) Foreign Application Priority Data
Jan. 19, 2020 (CN) .......................... 202010063033.6

(51) Int. Cl.
*C07D 215/22* (2006.01)
*A61K 9/20* (2006.01)

(52) U.S. Cl.
CPC .......... *C07D 215/22* (2013.01); *A61K 9/2013* (2013.01); *A61K 9/2018* (2013.01); *A61K 9/2059* (2013.01); *C07B 2200/13* (2013.01)

(58) Field of Classification Search
CPC ................................................... C07D 215/22
(Continued)

(56) References Cited

U.S. PATENT DOCUMENTS 10,208,065 B2 * 2/2019 Li et al. ............... C07D 519/00
546/83
11,161,817 B2 * 11/2021 Zhang et al. ........ C07D 215/48
(Continued)

FOREIGN PATENT DOCUMENTS

CN 109134365 * 1/2019 .......... C07D 215/48
CN 109134365 A * 5/2019 .......... C07D 215/48
(Continued)

OTHER PUBLICATIONS

Machine translation of CN109134365A, google patents, retrieved 2025. (Year: 2019).*
(Continued)

*Primary Examiner* — Jeffrey S Lundgren
*Assistant Examiner* — Heather R Dahlin
(74) *Attorney, Agent, or Firm* — Yue (Robert) Xu; Apex Attorneys at Law, LLP

(57) ABSTRACT

Disclosed in the present invention is a crystalline form of fluvatinib or fluvatinib methanesulfonate, and a preparation method therefor. The crystalline form I of the fluvatinib has characteristic diffraction peaks as shown in FIG. 1. The crystalline form of the fluvatinib methanesulfonate may take multiple forms, including seven crystalline forms, forms (Continued)

Exo Up                 Temperature (°C)

I-VII, wherein crystalline form III has characteristic diffraction peaks as shown in FIG. 9. Said crystalline forms are suited to manufacturing processes for fluvatinib methanesulfonate formulations.

4 Claims, 12 Drawing Sheets

(58) Field of Classification Search
USPC ........................................................ 514/312
See application file for complete search history.

(56) References Cited

U.S. PATENT DOCUMENTS

| | | |
|---|---|---|
| 2019/0218184 A1 | 7/2019 | Chen et al. |
| 2020/0262791 A1 | 8/2020 | Zhang et al. |

FOREIGN PATENT DOCUMENTS

| | | |
|---|---|---|
| EP | 3939592 A2 | 1/2022 |
| JP | 2018-520205 A | 7/2018 |
| JP | 2019-529414 A | 10/2019 |
| JP | 2019-529478 A | 10/2019 |
| WO | 2018196687 A1 | 11/2018 |
| WO | 2019/062637 A1 | 4/2019 |
| WO | 2020187188 A1 | 9/2020 |

OTHER PUBLICATIONS

First Office Action dated Jun. 13, 2023 for Japanese patent application No. 2022-543726, English translation provided by Global Dossier.

Denis Mangin et al., "Polymorphism in Processes of Crystallization in Solution: A Practical Review", Organic Process Research & Development 2009, 13, 1241-1253.

International Search Report for PCT/CN2021/081023 mailed Jun. 16, 2021, ISA/CN.

\* cited by examiner

CRYSTALLINE FORM OF FLUVATINIB OR FLUVATINIB METHANESULFONATE AND PREPARATION METHOD THEREFOR

This application is the national phase of International Application No. PCT/CN2021/081023, titled "CRYSTAL-LINE FORM OF FLUVATINIB OR FLUVATINIB METH-ANESULFONATE AND PREPARATION METHOD THEREFOR", which claims the priority to Chinese Patent Application No. 202010063033.6, titled "CRYSTALLINE FORM OF FLUVATINIB OR FLUVATINIB METHANE-SULFONATE AND PREPARATION METHOD THERE-FOR", filed on Jan. 19, 2020 with the China National Intellectual Property Administration, the entire disclosures thereof are incorporated herein by reference.

FIELD

The present disclosure relates to the field of medicinal chemistry, and specifically relates to a crystalline form of fluvatinib or fluvatinib mesylate and preparation method thereof.

BACKGROUND

Liver cancer is a common malignant tumor in China. The database reported by the National Cancer Center in 2017 showed that the number of new liver cancer cases reached 362,000, and the incidence rate ranked third in China; the number of liver cancer deaths reached 316,000, ranking second. Hepatocellular carcinoma (HCC) occurs insidiously without obvious symptoms in early stage, so most of patients have missed the opportunity for surgery when they are diagnosed. Surgery, interventional therapy and chemo-therapy all are not satisfactory for the treatment of liver cancer. Currently, 5-year survival rate of liver cancer is still very low.

Targeted drug therapy for HCC was born with the devel-opment of science and technology. The current target drugs for liver cancer mainly include epidermal growth factor receptor (EGFR) inhibitors, vascular endothelial growth factor receptor (VEGFR) antagonists, multikinase inhibi-tors, the PI3K/Akt/mTOR signaling pathway, hepatocyte growth factor receptor (Met) inhibitors, and TGFβ receptor inhibitors. Currently approved TKI-targeting drugs mainly include sorafenib, lenvatinib and regorafenib. Thus, thera-peutic drugs are very limited.

CN109134365 discloses an active compound or pharma-ceutically acceptable salt thereof that acts on multi-targets including VEGFR 1-3 types, fibroblast growth factor recep-tor 1-3 types, RET, Kit and PDGFR, having a chemical structural formula I:

I

Its chemical name is 4-(2-fluoro-3-chloro-(cyclopropy-laminocarbonyl)aminophenoxy)-7-methoxy-6-quinolin-ecarboxamide, and drug name is fluvatinib. The compound is highly active and provides a potential new treatment option for patients with tumors such as liver and kidney.

However, the inventors have found that the free base and pharmaceutically acceptable salts of fluvatinib, especially the methanesulfonate salt, all exhibit polymorphism, which greatly affects drug quality control, since different crystal-line forms have polymorphic properties, such as different stability, solubility, and druggability. Therefore, it needs to develop a crystalline form with good stability and druggabil-ity.

SUMMARY

The objective of the present disclosure is to provide a crystalline form of 4-(2-fluoro-3-chloro-(cyclopropylami-nocarbonyl)aminophenoxy)-7-methoxy-6-quinolinecarboxa-mide (fluvatinib represented by formula I) or a crystalline form of fluvatinib methanesulfonate salt.

I

The fluvatinib methanesulfonate (also called as "fluva-tinib mesylate", which refers to the same compound) is the compound represented by formula II,

II

According to the present disclosure, a crystalline form of fluvatinib is provided, and its X-ray powder diffraction pattern has characteristic diffraction peaks at 2θ degrees of 11.60±0.2°, 16.72±0.2°, and 20.25±0.2°, and further its X-ray powder diffraction pattern has characteristic diffrac-tion peaks at 2θ degrees of 8.28±0.2°, 11.60±0.2°, 15.42±0.2°, 16.72±0.2°, 20.25±0.2°, 21.81±0.2°, 22.36±0.2° and 24.08±0.2°.

According to the present disclosure, a crystalline form of fluvatinib mesylate is provided, and its X-ray powder dif-fraction pattern has characteristic diffraction peaks at 2θ degrees of 9.60±0.2°, 22.49±0.2° and 23.07±0.2°, and fur-ther its X-ray powder diffraction pattern has characteristic diffraction peaks at 2θ degrees of 10.74±0.2°, 16.79±0.2°, 17.51±0.2°, 18.50±0.2°, 20.64±0.2°, 20.85±0.2°, 21.51±0.2°, 23.73±0.2°, 24.84±0.2°, 26.51±0.2°, 27.05±0.2°, 27.88±0.2°, 28.60±0.2° and 29.74±0.2°.

According to the present disclosure, a crystalline form of fluvatinib mesylate is provided, and its X-ray powder diffraction pattern has characteristic diffraction peaks as shown in FIG. 6.

According to the present disclosure, a crystalline form of fluvatinib mesylate is provided, and its X-ray powder diffraction pattern has characteristic diffraction peaks at 2θ degrees of 6.28±0.2°, 10.65±0.2°, 17.87±0.2°, 19.48±0.2°, 23.57±0.2°, and 24.38±0.2°, and further its X-ray powder diffraction pattern has characteristic diffraction peaks at 2θ degrees of 10.25±0.2°, 14.44±0.2°, 15.28±0.2°, 18.91±0.2°, 19.98±0.2°, 20.86±0.2°, 21.77±0.2°, 22.78±0.2°, and 24.98±0.2°.

According to the present disclosure, a crystalline form of fluvatinib mesylate is provided, and its X-ray powder diffraction pattern has characteristic diffraction peaks as shown in FIG. 10.

According to the present disclosure, a crystalline form of fluvatinib mesylate is provided, and its X-ray powder diffraction pattern has characteristic diffraction peaks as shown in FIG. 11.

According to the present disclosure, a crystalline form of fluvatinib mesylate is provided, and its X-ray powder diffraction pattern has characteristic diffraction peaks as shown in FIG. 12.

According to the present disclosure, a crystalline form of fluvatinib mesylate is provided, and its X-ray powder diffraction pattern has characteristic diffraction peaks as shown in FIG. 13.

In another aspect, the present disclosure provides a method of preparing the crystalline form of fluvatinib mesylate, which comprises mixing fluvatinib mesylate with an organic solvent to obtain a mixed solution, stirring the mixed solution at a temperature greater than 20° C., filtering to obtain a solid, and drying the solid to obtain the crystalline form of fluvatinib mesylate.

Preferably, in the above-mentioned method of the present disclosure, the temperature is greater than 20° C. and less than 70° C.

Preferably, in the above-mentioned method of the present disclosure, the stirring is performed for at least 1 hour.

Preferably, in the above-mentioned method of the present disclosure, the stirring time is 2-48 hours.

Preferably, in the above-mentioned method of the present disclosure, the temperature is 20-30° C.

Preferably, in the above-mentioned method of the present disclosure, the organic solvent is selected from the group consisting of methanol, ethanol, acetone, THF, isopropanol, ethyl acetate, acetonitrile, cyclohexane, n-hexane, n-heptane, 1,4-dioxane, dichloromethane and a mixed solvent of any combination thereof.

More preferably, in the above-mentioned method of the present disclosure, the organic solvent is ethanol.

More preferably, in the above-mentioned method of the present disclosure, the temperature is 20-30° C., and the stirring time is at least 2 hours or at least 12 hours, or at least 16 hours, or at least 24 hours, or 48 hours.

More preferably, in the above-mentioned method of the present disclosure, the temperature is greater than 30° C. and less than 70° C., and the stirring time is 1-3 hours.

More preferably, in the above-mentioned method of the present disclosure, the temperature is 20-30° C., and the stirring time is 1-2 hours.

More preferably, in any one of the above-mentioned method of the present disclosure, the organic solvent is ethanol.

Optionally, in the above-mentioned method of the present disclosure, the organic solvent can be a mixed solvent containing water, and preferably, can be a mixed solvent of ethanol and water or a mixed solvent of THF and water.

In the above-mentioned method of the present disclosure, different crystalline forms of fluvatinib mesylate may be obtained by controlling the process.

In some specific embodiments, the following embodiments are provided:

In an embodiment, a crystalline form I of fluvatinib of the present disclosure is provided, wherein its X-ray powder diffraction pattern has characteristic diffraction peaks at 2θ degrees of 11.60±0.2°, 16.72±0.2°, and 20.25±0.2°.

Further, the crystalline form I of fluvatinib exhibits an X-ray powder diffraction pattern having characteristic diffraction peaks at 2θ degrees of 8.28±0.2°, 11.60±0.2°, 15.42±0.2°, 16.72±0.2°, 20.25±0.2°, 21.81±0.2°, 22.36±0.2° and 24.08±0.2°.

Preferably, the crystalline form I of fluvatinib exhibits an X-ray powder diffraction pattern having characteristic diffraction peaks as shown in FIG. 1.

In some embodiments, the present disclosure provides a method of preparing the crystalline form I of fluvatinib, which comprises dissolving fluvatinib in an organic solvent to form a suspension, stirring, and filtering to obtain the crystalline form I. Preferably, the organic solvent is selected from the group consisting of methanol, ethanol, acetone, THF, isopropanol, ethyl acetate and any mixed solvent thereof.

In an embodiment, the present disclosure provides a crystalline form I of fluvatinib mesylate, which exhibits an X-ray powder diffraction pattern having characteristic diffraction peaks at 2θ degrees of 9.60±0.2°, 22.49±0.2° and 23.07±0.2°.

Further, the above-mentioned crystalline form I of fluvatinib mesylate exhibits an X-ray powder diffraction pattern having characteristic diffraction peaks at 2θ (±0.2°) degrees of 10.74, 16.79, 17.51, 18.50, 20.64, 20.85, 21.51, 23.73, 24.84, 26.51, 27.05, 27.88, 28.60 and 29.74.

Preferably, the crystalline form I of fluvatinib mesylate exhibits an X-ray powder diffraction pattern having characteristic diffraction peaks as shown in FIG. 4.

In some embodiments, the present disclosure further provides a method of preparing the crystalline form I of fluvatinib mesylate, which comprises dissolving fluvatinib in an organic solvent, adding methanesulfonic acid to perform a reaction, after the complete of the reaction, stirring at 20-30° C. for 1-2 hours, filtering, and drying. Preferably, the organic solvent is selected from the group consisting of methanol, ethanol, acetone, THF, isopropanol, ethyl acetate and a mixed solvent of any combination thereof. The drying includes drying under reduced pressure at a drying temperature of 40-50° C.

In an embodiment, the present disclosure provides a crystalline form II of fluvatinib mesylate, which exhibits an X-ray powder diffraction pattern having characteristic diffraction peaks at 2θ (±0.2° degrees of 4.88±0.2°, 6.93±0.2°, 9.77±0.2°, and 10.93±0.2°, and further exhibits an X-ray powder diffraction pattern having characteristic diffraction peaks at 2θ (±0.2°) degrees of 12.07, 14.81, 15.56, 17.72, 18.56, 19.74, 21.11, 21.73, 22.73, 24.68, 25.70, 6.19 and 27.49±0.2°.

Preferably, the crystalline form II of fluvatinib mesylate exhibits an X-ray powder diffraction pattern having characteristic diffraction peaks as shown in FIG. 6.

In some embodiments, the present disclosure further provides a method of preparing the crystalline form II of fluvatinib mesylate, which comprises reacting fluvatinib with a methanesulfonate salt in an organic solvent, stirring at 10-20° C. for 2 hours for solid precipitation, filtering, and drying.

In the above-mentioned method of the present disclosure, the organic solvent includes, but are not limited to methanol, ethanol, acetone, THF and isopropanol.

In another embodiment, the present disclosure provides a crystalline form III of fluvatinib mesylate, which exhibits an X-ray powder diffraction pattern having characteristic diffraction peaks at 2θ degrees of 6.28±0.2°, 10.65±0.2°, 17.87±0.2°, 19.48±0.2°, 23.57±0.2°, and 24.38±0.2°.

Further, the above-mentioned crystalline form III of fluvatinib mesylate further exhibits an X-ray powder diffraction pattern having characteristic diffraction peaks at 2θ degrees of 10.25±0.2°, 14.44±0.2°, 15.28±0.2°, 18.91±0.2°, 19.98±0.2°, 20.86±0.2°, 21.77±0.2°, 22.78±0.2°, and 24.98±0.2°.

Preferably, the above-mentioned crystalline form III of fluvatinib mesylate of the present disclosure exhibits an X-ray powder diffraction pattern having characteristic diffraction peaks as shown in FIG. 8.

In some embodiments, the present disclosure further provides a method of preparing the crystalline form III of fluvatinib mesylate, which comprises stirring fluvatinib mesylate in an organic solvent for at least 2 hours.

In some specific embodiments, the above-mentioned method of preparing the crystalline form III of fluvatinib mesylate comprises dissolving fluvatinib mesylate in an organic solvent, stirring at 20-30° C. for at least 12 hours, preferably at least 16 hours, 24 hours or 48 hours, filtering, and drying filter cake.

In some specific embodiments, the above-mentioned method of preparing the crystalline form III of fluvatinib mesylate comprises dissolving fluvatinib mesylate in an organic solvent, stirring at 30-65° C. for 2-3 hours, filtering, and drying filter cake.

In the above-mentioned method of the present disclosure, the drying includes drying under reduced pressure at a drying temperature of 40-50° C. The organic solvent is selected from the group consisting of ethanol, methanol, isopropanol, acetone, THF, cyclohexane, n-hexane, n-heptane, 1,4-dioxane, dichloromethane and ethyl acetate, and preferably from ethanol, acetone or ethyl acetate.

Further, in the present disclosure, a crystalline form IV of fluvatinib mesylate is provided, and its X-ray powder diffraction pattern has characteristic diffraction peaks at 2θ (±0.2°) degrees of 6.22±0.2°, 10.59±0.2°, 11.58±0.2°, 14.41±0.2°, 17.93±0.2°, 20.32±0.2°, 23.58±0.2°, 24.09±0.2°, 24.59±0.2°, and 25.79±0.2°, and preferably, its X-ray powder diffraction pattern has characteristic diffraction peaks as shown in FIG. 10.

The present disclosure provides a method of preparing the crystalline form IV of fluvatinib mesylate, which comprises dissolving fluvatinib methanesulfonate salt in a mixed solvent system of ethanol/water, stirring at 20-30° C. for 20-48 h, filtering, and spin-drying filter cake at 40-50° C. under reduced pressure, to obtain the crystalline form IV of fluvatinib mesylate.

In the present disclosure, a crystalline form V of fluvatinib mesylate is further provided, and its X-ray powder diffraction pattern has characteristic diffraction peaks at 2θ degrees of 4.81±0.2°, 10.64±0.2°, 10.99±0.2°, 16.00±0.2°, 20.50±0.2°, 21.10±0.2°, 24.59±0.2°, 25.57±0.2° and 26.46±0.2°, and preferably its X-ray powder diffraction pattern has characteristic diffraction peaks as shown in FIG. 11.

The present disclosure provides a method of preparing the crystalline form V of fluvatinib mesylate, which comprises dissolving fluvatinib methanesulfonate salt in a mixed solvent system of tetrahydrofuran/water, stirring at 20-30° C. for 20-48 h, filtering, and spin-drying filter cake at 40-50° C. under reduced pressure, to obtain the crystalline form V of fluvatinib mesylate.

The present disclosure further provides a crystalline form VI of fluvatinib mesylate, wherein its X-ray powder diffraction pattern has characteristic diffraction peaks at 2θ (±0.2° degrees of 5.61±0.2°, 9.98±0.2°, 10.61±0.2°, 16.84±0.2°, 20.14±0.2°, and 20.89±0.2°, and preferably its X-ray powder diffraction pattern has characteristic diffraction peaks as shown in FIG. 12.

The present disclosure provides a method of preparing the crystalline form VI of fluvatinib mesylate, which comprises adding fluvatinib free base into methanol solvent, and adding methanesulfonic acid under stirring to perform a reaction. The reaction solution is stirred at 20-30° C. for 2-10 h, and preferably for 4 h, filtering, and spin-drying filter cake at 40-50° C. under reduced pressure, to obtain the crystalline form VI of fluvatinib mesylate.

The present disclosure further provides a crystalline form VII of fluvatinib mesylate, wherein its X-ray powder diffraction pattern has characteristic diffraction peaks at 2θ degrees of 5.57±0.2°, 6.17±0.2°, 9.93±0.2°, 10.56±0.2°, 14.34±0.2°, 16.81±0.2°, 17.76±0.2°, 20.10±0.2°, 20.81±0.2°, 24.85±0.2°, and 25.60±0.2°, and preferably its X-ray powder diffraction pattern has characteristic diffraction peaks as shown in FIG. 13.

The present disclosure provides a method of preparing the crystalline form VII of fluvatinib mesylate, which comprises dissolving the crystalline form VI of fluvatinib mesylate into ethanol solvent, stirring at 20-30° C. for 2-10 h, filtering, and spin-drying filter cake at 40-50° C. under reduced pressure, to obtain the crystalline form VII of fluvatinib mesylate.

The present disclosure also provides use of the above-mentioned crystalline form I of fluvatinib and crystalline forms I, II, III, IV, V, VI, VII of fluvatinib mesylate in the manufacture of a medicament for treating a tumor, wherein the tumor includes, but are not limited to liver cancer, renal carcinoma, gastric cancer, colorectal cancer, pancreatic cancer and lung cancer.

The present disclosure further provides a pharmaceutical composition containing an effective amount of the above-mentioned crystalline form of fluvatinib or fluvatinib mesylate according to the present disclosure and a pharmaceutically acceptable adjuvant, wherein the crystalline form is selected from the crystalline form I of fluvatinib and the crystalline form I, II, III, IV, V, VI and VII of fluvatinib mesylate. Preferably, the crystalline form is crystalline form I or crystalline form III of fluvatinib mesylate.

In the above-mentioned composition of the present disclosure, the adjuvant includes, but is not limited to, a filler, a disintegrating agent, an adhesive, a lubricant, a coloring agent, a flavoring agent, an emulsifier, surfactant, a cosolvent, a suspending agent, an isotonic agent, a buffer, a preservative, an antioxidant, a stabilizer, an absorption enhancer and the like. The above-mentioned adjuvants may be appropriately combined for use, depending on the different formulation forms of the composition.

Specifically, the above-mentioned filler is selected from the group consisting of lactose, white sugar, glucose, corn starch, mannitol, sorbitol, starch, α-starch, dextrin, crystalline cellulose, light anhydrous silicic acid, aluminum silicate, calcium silicate, magnesium aluminum silicate, calcium hydrogen phosphate and combinations thereof. The above-mentioned disintegrating agent is selected from the group consisting of crystalline cellulose, agar, gelatin, calcium carbonate, sodium bicarbonate, calcium citrate, dextrin, pectin, low-substituted hydroxypropyl cellulose, carboxymethyl cellulose, carboxymethylcellulose calcium, croscarmellose sodium, carboxymethyl starch, sodium carboxymethyl starch and combinations thereof. The above-mentioned adhesive is selected from the group consisting of polyvinyl alcohol, methylcellulose, ethyl cellulose, gum arabic, gum tragacanth, gelatin, shellac, hydroxypropyl methylcellulose, hydroxypropyl cellulose, carboxy methyl cellulose sodium, polyvinylpyrrolidone, polyethylene glycol and combinations thereof. The above-mentioned lubricant is selected from the group consisting of magnesium stearate, calcium stearat, sodium octadecyl fumarate, talc, polyethylene glycol, colloidal silica, and combinations thereof. The above-mentioned coloring agent is selected from the group consisting of ferric oxide, yellow ferric oxide, carmine, caramel, β-carotene, titanium oxide, talc, sodium riboflavin phosphate, yellow aluminum lake, and other medical colorants. The above-mentioned flavoring agent is selected from the group consisting of cocoa powder, menthol, aromatic powder, peppermint oil, borneol, and cinnamon powder. The above-mentioned surfactant is selected from the group consisting of octadecyl triethanolamine, sodium dodecyl sulfate, lauryl aminopropionic acid, lecithin, glycerol monostearate, sucrose fatty acid ester, and glycerol fatty acid ester. The above-mentioned cosolvent is selected from the group consisting of polyethylene glycol, propylene glycol, benzyl benzoate, ethanol, cholesterol, triethanolamine, sodium carbonate, sodium citrate, and Tween 80.

The above-mentioned antioxidant may be a sulfite, ascorbic acid, α-tocopherol or the like.

In the present disclosure, the above-mentioned composition may be in a formulation form including tablets, powders, granules, capsules, syrup, buccal tablets, inhalants and other oral preparations, or injections.

The above-mentioned oral preparation may be coated on their surfaces, if needed.

The above injections may be supplemented with appropriate additives, such as emulsifiers, surfactants, cosolvents, suspending agents, isotonic agents, buffers, preservatives, antioxidants, stabilizers, absorption enhancers.

When the crystals of the present disclosure are used as a drug, an adult may be typically administered 100 μg to 10 g per day in one or several divided doses, depending on symptoms, age, and administration mode.

The crystalline forms of the present disclosure are very useful as an angiogenesis inhibitor, and can effectively treat or prevent diseases though its angiogenesis inhibitory action, e.g., as an angiogenesis inhibitor, an antitumor agent, a hemangioma therapeutic agent, or a cancer metastasis inhibitor.

Moreover, when the above-mentioned composition of the present disclosure is used as an antitumor agent, the tumor includes liver cancer, pancreatic cancer, gastric cancer, thyroid carcinoma, colorectal cancer, breast cancer, prostate cancer, lung cancer, renal carcinoma, brain tumor, blood cancer or ovarian cancer, and preferably is liver cancer, thyroid carcinoma, gastric cancer, colorectal cancer, prostate cancer, lung cancer or renal carcinoma.

The crystalline forms of fluvatinib according to the present disclosure, which has never been reported, had been kept under high temperature and high humidity conditions for half of a month or 3 months to investigate its stability, and the results showed no occurrence of crystal transformation and no change on the content of related impurities. In addition, when it was stirred in an organic solvent, e.g., methanol, ethanol, acetone, THF, isopropanol, ethyl acetate or their mixed solvent with water for at least 2 days, no crystal transformation occurred, indicating that it is stable in solvents including water, and thus is conducive to adapt to the processing of its preparations.

The crystalline forms of the fluvatinib mesylate of present disclosure exhibit typical polymorphism, including the seven crystalline forms found in the present disclosure. Among them, crystalline forms I and III exhibit superior specific characteristics, for example, when they were placed under the harsh experimental conditions of high temperature and high humidity for at least half of a month or 3 months to investigate its stability, the crystalline forms I and III of fluvatinib mesylate did not show crystal transformation, and no apparent change occurred on the related substance contents compared with before, exhibiting physical and chemical stabilities. In particular, the crystalline form III exhibits good formulation manufacturing characteristics such as good fluidity, hygroscopicity, and the like.

After the crystalline form II, crystalline form III, crystalline form VI, crystalline form VII of fluvatinib mesylate were stirred in ethanol for 2-4 days, the crystalline form II, crystalline form VI, crystalline form VII of fluvatinib mesylate were all transformed into the crystalline form III, whereas the crystalline form III did not undergo crystal transformation under this condition, indicating that the crystalline form III has better stability than the crystalline forms II, VI and VII, and more suitable and adaptable to formulation processing process. And, its solubility is better than that of lenvatinib.

DETAILED DESCRIPTION

The following examples are only illustrative and are given to further describe or aid in understanding the spirit of the present invention, but do not limit the scope of the present invention in any way, and any simple modifications within the scope of the spirit of the present invention also fall within the scope of the present invention.

In this disclosure, parameters of the crystalline forms were measured by X-ray powder diffraction pattern (XRPD), DSC and TGA, which are commonly used in the ar. The instruments specifically used are set forth as follows. Based on the instruments and errors resulted from test, the result has an error ranging within ±0.2 in XRPD.

X-Ray Powder Diffraction (XRPD)

Model: Bruker D8 advance X-ray powder diffractometer

Test method: approximately 10-20 mg sample for XRPD detection

The detailed XRPD parameters are as follows:

Light tube: Cu, kα, (λ=1.54056 Å).

Light tube voltage: 40 kV, light tube current: 40 mA

Divergence slit: 0.60 mm

Detector slit: 10.50 mm

Anti-scatter slit: 7.10 mm

Scanning range: 4-40 deg

Step: 0.02 deg

Step size: 0.12 sec.

Differential Scanning Calorimeter (DSC)

Test condition: about 0.5-1 mg of sample for DSC detection

Method: the sample was heated from the room temperature to 300° C. or to 350° C. at a heating rate of 10° C./min in $N_2$ at 50 mL/min.

Thermogravimetric Analyzer (TGA)

Test conditions: about 2-5 mg of samples for TGA detection

Method: the sample was heated from the room temperature to have a weight loss of 20% or to 300° C. at a heating rate of 10° C./min in $N_2$ at 25 mL/min.

| Dynamic Vapor Sorption (DVS) | |
| --- | --- |
| Temperature | 25° C. |
| Amount of the sample | 10-30 mg |
| Protective gas and flow rate | $N_2$, 200 mL/min |
| dm/dt | 0.002%/min |
| Minimum dm/dt equilibration time | 10 min |
| Maximum equilibration time | 180 min |

-continued

| Dynamic Vapor Sorption (DVS) | |
| --- | --- |
| RH range | 0% RH-95% RH-0% RH 10% (90% RH-0% RH-90% RH) |
| RH gradient | 5% (95% RH-90% RH and 90% RH-95% RH) |

The sample was placed on a glass slide, and observed after being dispersed with a cover glass. Objective lens: 20/50 times.

Hereinafter, the present the present disclosure will be further described in conjunction with examples.

Example 1 Preparation of Crystalline Form I of Fluvatinib

Figures 1, 2:
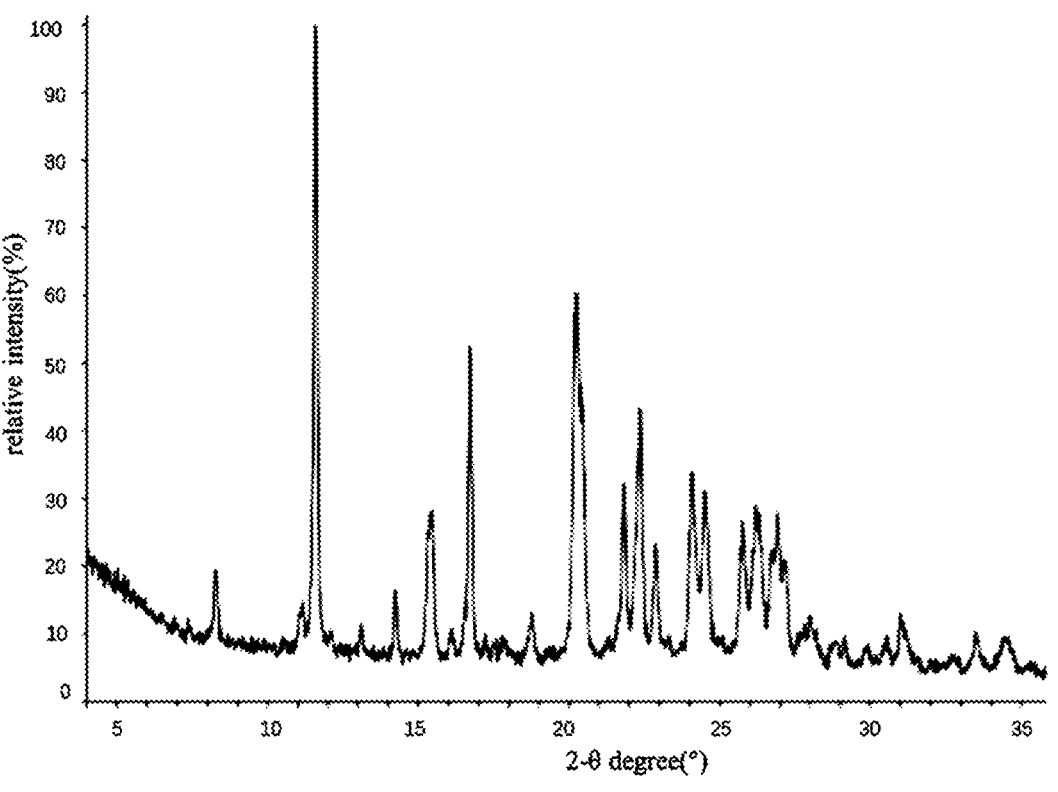
FIG. 1 is XRPD pattern of the crystalline form I of fluvatinib.
FIG. 2 is DSC curve of the crystalline form I of fluvatinib.
Figure 3:
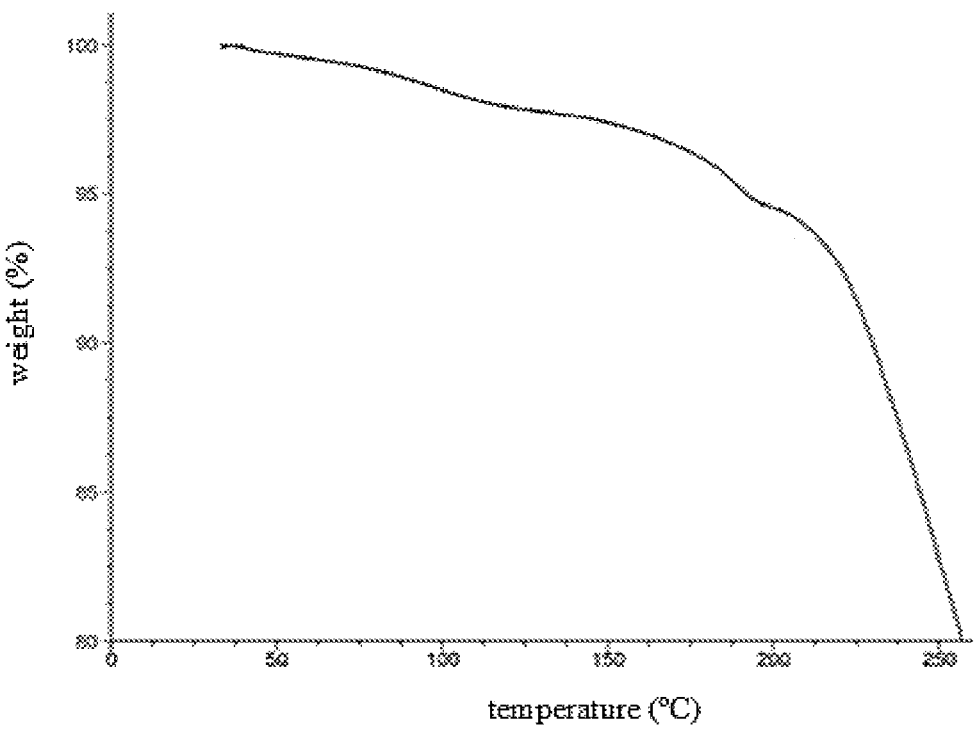
FIG. 3 is TGA curve of the crystalline form I of fluvatinib.

The free base of fluvatinib of formula I (50 mg, 112.40 umol) was added into EtOH (2 mL), stirred at 15-20° C. for 12 h, filtered to obtain a filter cake. The filter cake was added to 200 mL of acetone, stirred at 15-20° C. for 12 h, and filtered. The filter cake was dried at 40° C. with spinning under reduced pressure, to obtain a fluvatinib solid, named as crystalline form I of fluvatinib. Its XRPD result is shown in FIG. 1, and its DSC and TGA test results are shown in FIG. 2 and FIG. 3.

Example 2 Preparation of the Crystalline Form I of the Fluvatinib Methanesulfonate (Also Called as "Fluvatinib Mesylate" Herein)

Figure 4:
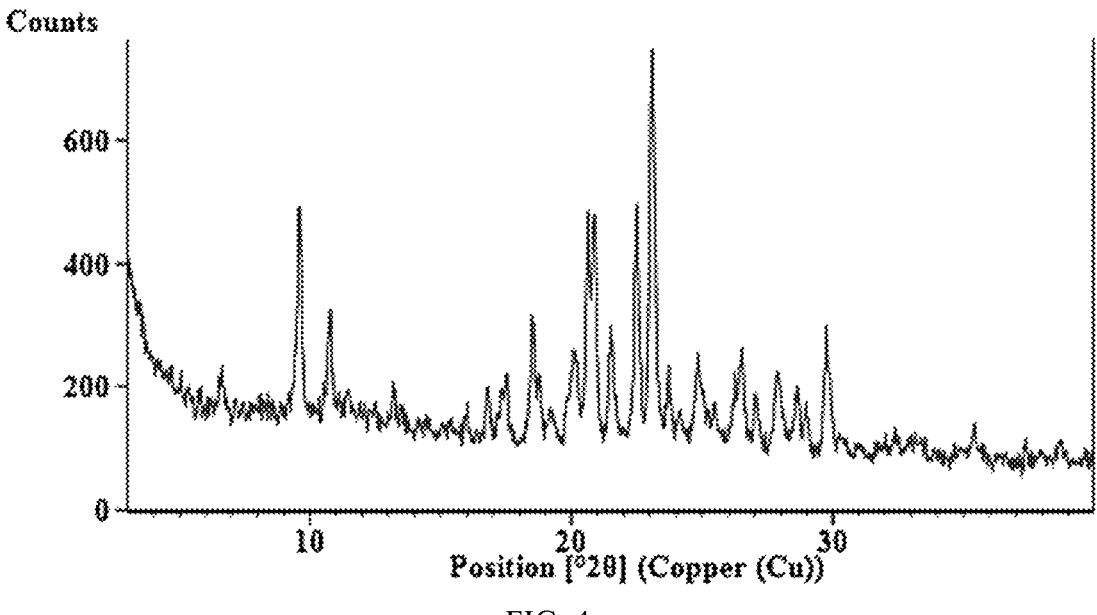
FIG. 4 is XRPD pattern of the crystalline form I of fluvatinib mesylate.
Figure 5:
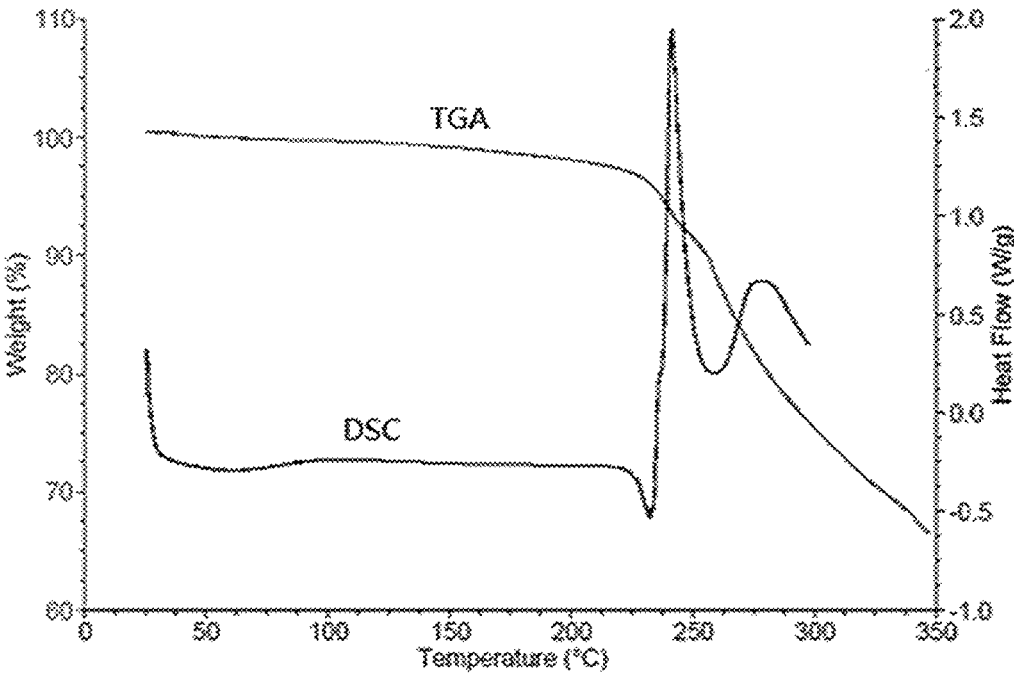
FIG. 5 is DSC and TGA curves of the crystalline form I of fluvatinib mesylate.

4-[3-chloro-4-(cyclopropylaminocarbonylamino)-2-fluoro-phenoxy]-7-methoxy-quinoli ne-6-carboxamide, that is, fluvatinib (0.5 g, 1.12 mmol) was added to EtOH (10 mL) solvent, heated to 55-60° C. At this temperature, methanesulfonic acid (108.02 mg, 1.12 mmol, 80.02 μL, 1 eq) was added to the reaction flask under stirring. When the reaction solution became clear, the reaction solution was cooled to 20-30° C., stirred at this temperature for 1 h when a brown solid was precipitated, and filtered under reduced pressure. The filter cake was rinsed with ethanol (2 mL×2), and dried at 40-50° C. with spinning under reduced pressure, to obtain a solid product, named as the crystalline form I of fluvatinib mesylate. The product was detected by XRPD, DSC, and TGA. The XRPD test results are shown in Table 1 and FIG. 4. The DSC and TGA test results are shown in FIG. 5. The melting point was about 232-237° C.

TABLE 1

| XRPD diffraction data of the crystalline form I of fluvatinib mesylate | | | | |
| --- | --- | --- | --- | --- |
| Pos. [°2θ] | Height [cts] | FWHM Left [°2θ] | d-spacing [Å] | Rel. Int. [%] |
| 6.61 | 49.82 | 0.3070 | 13.37 | 7.82 |
| 9.59 | 336.03 | 0.1279 | 9.22 | 52.76 |
| 10.74 | 149.30 | 0.1535 | 8.24 | 23.44 |
| 16.79 | 81.84 | 0.2047 | 5.28 | 12.85 |
| 17.41 | 76.72 | 0.3070 | 5.09 | 12.04 |
| 18.52 | 192.97 | 0.1279 | 4.79 | 30.30 |
| 20.12 | 143.50 | 0.2047 | 4.41 | 22.53 |
| 20.64 | 374.14 | 0.1279 | 4.30 | 58.74 |
| 20.86 | 357.93 | 0.1279 | 4.26 | 56.19 |
| 21.54 | 160.09 | 0.1791 | 4.13 | 25.13 |
| 22.50 | 390.36 | 0.1535 | 3.95 | 61.29 |
| 23.09 | 636.96 | 0.2047 | 3.85 | 100.00 |
| 23.72 | 116.62 | 0.1535 | 3.75 | 18.31 |
| 24.84 | 140.89 | 0.2047 | 3.58 | 22.12 |

TABLE 1-continued

| Pos. [°2θ] | Height [cts] | FWHM Left [°2θ] | d-spacing [Å] | Rel. Int. [%] |
|---|---|---|---|---|
| | | XRPD diffraction data of the crystalline form I of fluvatinib mesylate | | |
| 26.50 | 149.71 | 0.2047 | 3.36 | 23.50 |
| 27.06 | 80.66 | 0.2047 | 3.29 | 12.66 |
| 27.89 | 122.65 | 0.2558 | 3.20 | 19.26 |
| 28.63 | 93.67 | 0.1535 | 3.12 | 14.71 |
| 29.78 | 166.56 | 0.3070 | 3.00 | 26.15 |
| 35.35 | 27.07 | 0.6140 | 2.54 | 4.25. |

Example 3 Preparation of the Crystalline Form II of Fluvatinib Mesylate

Figure 6:
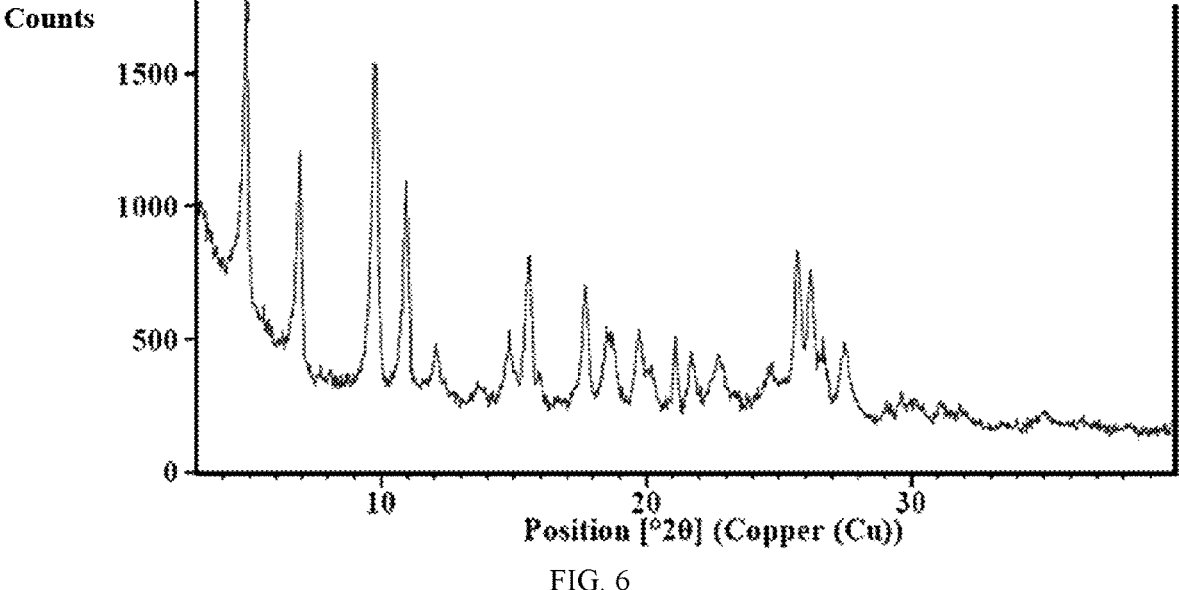
FIG. 6 is XRPD pattern of the crystalline form II of fluvatinib mesylate.
Figure 7:
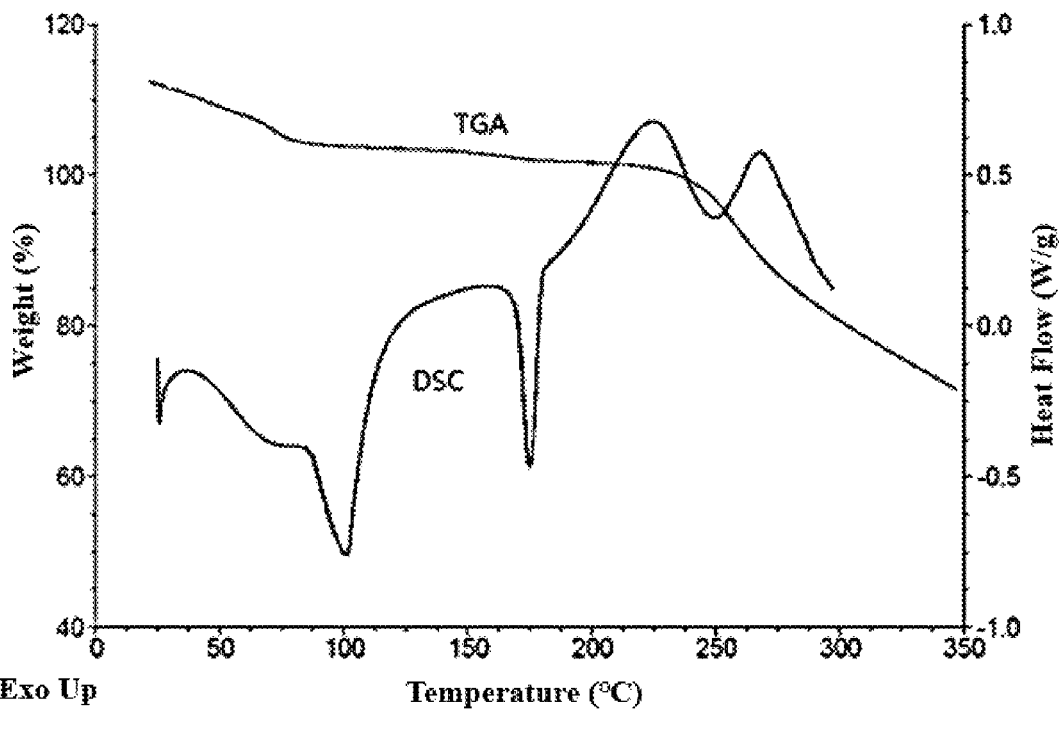
FIG. 7 is DSC and TGA curves of the crystalline form II of fluvatinib mesylate.

The free base fluvatinib (55 g) was added to EtOH (1.1 L) solvent, heated to 55-60° C. The methanesulfonic acid (11.88 g) was added to the reaction flask under stirring (300 rpm), and cooled to 10-20° C. after the complete of the reaction. The reaction system was stirred at this temperature for 2 h when a brown solid precipitated, and filtered at reduced pressure. The filter cake was rinsed with ethanol (50 mL×2), dried at 40-50° C. with spinning under reduced pressure to obtain a product, which was a brown solid crystalline form (52.5 g). The product was detected by XRPD, TGA, and DSC, and named as the crystalline form II of fluvatinib mesylate (Form II). The results are shown in Table 2, FIG. 6 and FIG. 7.

TABLE 2

| Pos. [°2θ] | Height [cts] | FWHM Left [°2θ] | d-spacing [Å] | Rel. Int. [%] |
|---|---|---|---|---|
| | | XRPD diffraction data of the crystalline form II of fluvatinib mesylate | | |
| 4.88 | 1134.08 | 0.1023 | 18.09 | 93.20 |
| 6.93 | 796.51 | 0.1279 | 12.76 | 65.46 |
| 9.77 | 1216.83 | 0.1791 | 9.05 | 100.00 |
| 10.93 | 760.87 | 0.2047 | 8.10 | 62.53 |
| 12.07 | 182.42 | 0.2047 | 7.33 | 14.99 |
| 14.81 | 242.22 | 0.2047 | 5.98 | 19.91 |
| 15.56 | 546.79 | 0.1535 | 5.69 | 44.94 |
| 17.72 | 446.01 | 0.1791 | 5.01 | 36.65 |
| 18.56 | 261.42 | 0.2558 | 4.78 | 21.48 |
| 19.74 | 282.58 | 0.2047 | 4.50 | 23.22 |
| 21.11 | 272.39 | 0.1279 | 4.21 | 22.39 |
| 21.73 | 188.45 | 0.1535 | 4.09 | 15.49 |
| 22.73 | 211.49 | 0.3070 | 3.91 | 17.38 |
| 24.68 | 164.93 | 0.3070 | 3.61 | 13.55 |
| 25.70 | 612.62 | 0.1791 | 3.47 | 50.35 |
| 26.19 | 535.08 | 0.1791 | 3.40 | 43.97 |
| 27.49 | 268.24 | 0.2814 | 3.24 | 22.04 |
| 34.99 | 43.59 | 0.6140 | 2.56 | 3.58. |

Example 4 Preparation of the Crystalline Form III of Fluvatinib Mesylate

Figure 8:
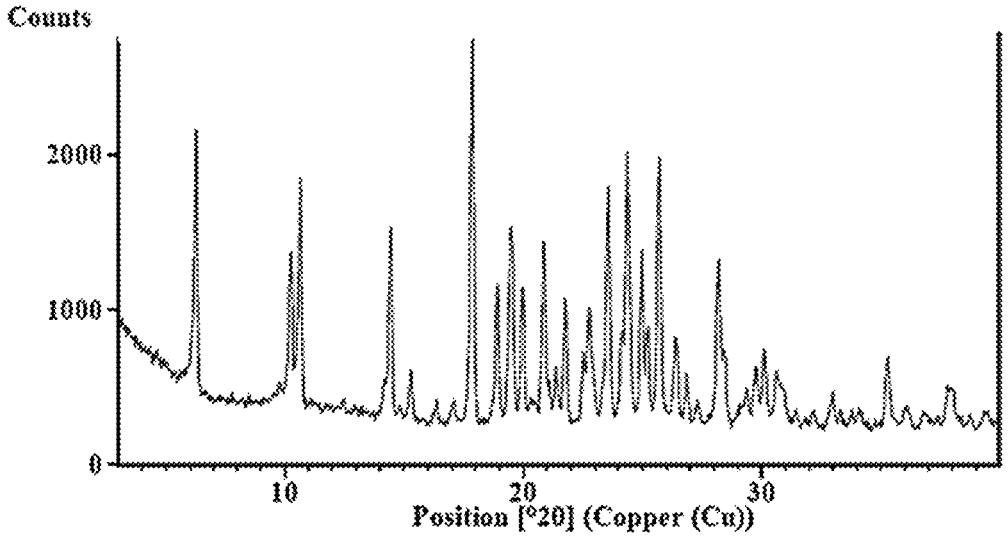
FIG. 8 is XRPD pattern of the crystalline form III of fluvatinib mesylate.
Figures 9, 10:
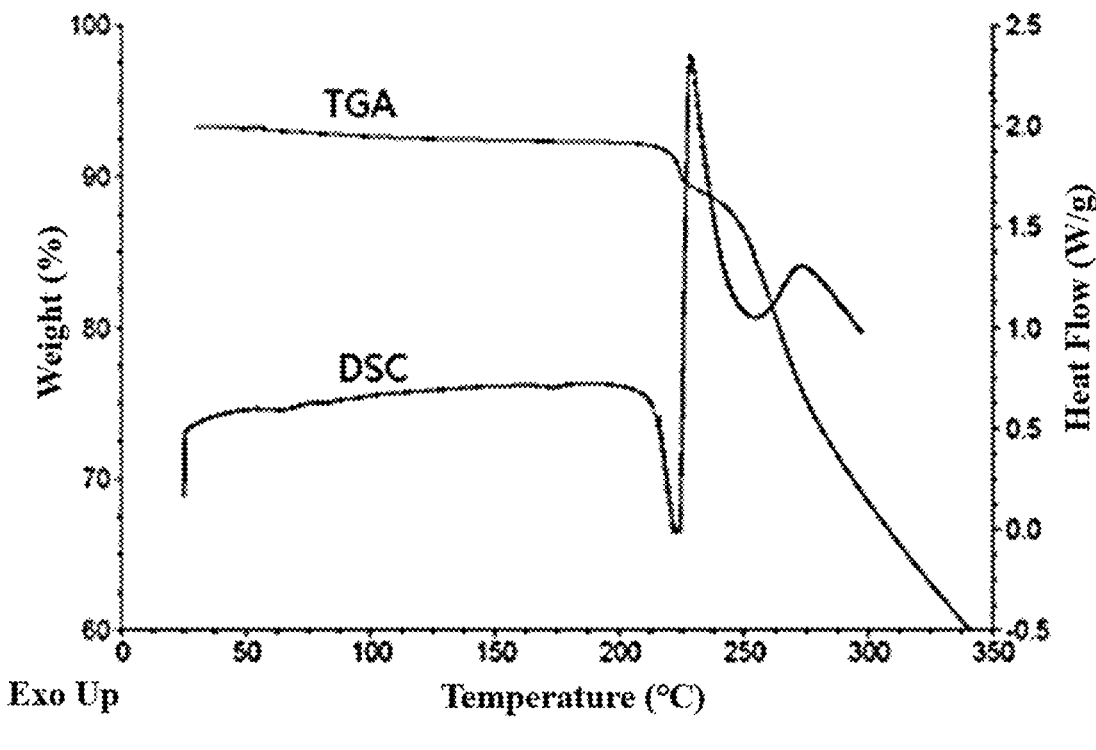
FIG. 9 is DSC and TGA curves of the crystalline form III of fluvatinib mesylate.
FIG. 10 is XRPD pattern of the crystalline form IV of fluvatinib mesylate.

Method 1: To a reaction flask, 100 g of fluvatinib (free base) was added to MeOH (2.2 L) solvent, and then methanesulfonic acid (16.64 mL) was added under stirring into the reaction flask to perform a reaction. The mixture was stirred at 20-30° C. for 4 h when a brown solid precipitated, and filtered at reduced pressure. The filter cake was rinsed with ethanol (50 mL×2), and dried at 40-50° C. with spinning under reduced pressure to obtain a solid product (106.2 g). The solid product (105 g) was added to 1 L of ethanol in a reaction flask, stirred at 20-30° C. for 48 h, and filtered at reduced pressure, to obtain a filter cake. The filter cake was dried at 40-50° C. under reduced pressure to obtain a solid crystalline product. The product was detected by XRPD, TGA, and DSC. The results are shown in Table 3, FIG. 8 and FIG. 9. The XRPD data show that the crystalline form of the product was the crystalline form III of fluvatinib mesylate (Form III). Its melting point was about 220-226° C.

Method 2: The crystalline form II of fluvatinib mesylate (52 g) obtained in Example 3 was added to 420 mL of ethanol, stirred mechanically at 20-30° C. (300 rpm) for 16 h, and filtered at reduced pressure. The filter cake was dried at 40-50° C. under reduced pressure to obtain a product. The product was detected by XRPD. As a result, its 2θ degrees in XRPD are basically consistent with those in FIG. 8, indicating that the obtained crystalline form is Form III.

Method 3: 0.5 g of fluvatinib free base was added to 10 mL of ethanol, and added with 0.1 mL of methanesulfonic acid. The mixture was suspended at 40° C. for 3-4 hours, centrifuged, filtered, and dried at 40° C. in an oven. The detection results show that the prepared product is crystalline form III of the methanesulfonate salt. Its 2θ degrees in XRPD are basically consistent with those in FIG. 8.

Method 4: 0.9 g of fluvatinib methanesulfonate was added to 7.2 mL of ethanol in a reaction flask under stirring. After the addition, the mixture was heated to 55-65° C., stirred at this temperature for about 2-3 h, and filtered at reduced pressure. The filter cake was rinsed with ethanol (0.5 mL×2) to obtain a filter cake, and dried at 45° C. under vacuum to obtain a product. Its 2θ degrees in XRPD are basically consistent with those in FIG. 8.

TABLE 3

| Pos. [°2θ] | Height [cts] | FWHM Left [°2θ] | d-spacing [Å] | Rel. Int. [%] |
|---|---|---|---|---|
| | | XRPD diffraction data of the crystalline form III of fluvatinib mesylate | | |
| 6.28 | 1707.03 | 0.1023 | 14.09 | 67.71 |
| 10.25 | 983.92 | 0.1279 | 8.63 | 39.03 |
| 10.64 | 1502.23 | 0.1279 | 8.31 | 59.59 |
| 14.44 | 1215.18 | 0.1279 | 6.13 | 48.20 |
| 15.28 | 314.50 | 0.1023 | 5.80 | 12.47 |
| 16.34 | 103.69 | 0.1535 | 5.43 | 4.11 |
| 17.06 | 129.56 | 0.2047 | 5.20 | 5.14 |
| 17.87 | 2521.11 | 0.1535 | 4.97 | 100.00 |
| 18.91 | 899.67 | 0.1279 | 4.69 | 35.69 |
| 19.48 | 1268.38 | 0.2303 | 4.56 | 50.31 |
| 19.98 | 880.05 | 0.1279 | 4.44 | 34.91 |
| 20.86 | 1181.20 | 0.1279 | 4.26 | 46.85 |
| 21.39 | 288.79 | 0.1023 | 4.15 | 11.45 |
| 21.77 | 810.45 | 0.1279 | 4.08 | 32.15 |
| 22.54 | 460.84 | 0.1023 | 3.94 | 18.28 |
| 22.78 | 742.06 | 0.1279 | 3.90 | 29.43 |
| 23.57 | 1537.53 | 0.1791 | 3.78 | 60.99 |
| 24.38 | 1757.30 | 0.1535 | 3.65 | 69.70 |
| 24.98 | 1119.25 | 0.1279 | 3.56 | 44.40 |
| 25.23 | 621.29 | 0.1023 | 3.53 | 24.64. |

Example 5 Preparation of the Crystalline Form IV of Fluvatinib Mesylate

About 1.0 g of fluvatinib methanesulfonate was weighed and added to a mixed solvent system of 4 mL ethanol/4 mL water (1:1), to form a suspension. The suspension sample was stirred using a magnetic stirrer (20-30° C.) and became a brown suspension after 48 h, and filtered under reduced pressure. The filter cake was dried at 40-50° C. with spinning under reduced pressure, to obtain 625 mg of a dry solid crystalline product, with a yield of 62.5%. The product was detected by XRPD. The results shown in Table 4 and FIG. 10 indicate that the product is the crystalline form IV of fluvatinib mesylate.

TABLE 4

| | XRPD diffraction data of the crystalline form IV of fluvatinib mesylate | | | |
|---|---|---|---|---|
| Pos. [°2θ] | Height [cts] | FWHM Left [°2θ] | d-spacing [Å] | Rel. Int. [%] |
| 6.22 | 1265.67 | 0.1535 | 14.22 | 67.64 |
| 8.29 | 319.16 | 0.1535 | 10.67 | 17.06 |
| 10.59 | 1692.34 | 0.1535 | 8.35 | 90.44 |
| 11.58 | 1224.15 | 0.1023 | 7.64 | 65.42 |
| 13.06 | 76.40 | 0.3070 | 6.78 | 4.08 |
| 14.41 | 993.01 | 0.1535 | 6.14 | 53.07 |
| 15.35 | 347.84 | 0.1535 | 5.77 | 18.59 |
| 15.52 | 279.28 | 0.1535 | 5.71 | 14.93 |
| 16.73 | 498.57 | 0.1023 | 5.30 | 26.64 |
| 17.93 | 1090.31 | 0.1279 | 4.95 | 58.27 |
| 18.84 | 815.02 | 0.1023 | 4.71 | 43.56 |
| 19.56 | 583.03 | 0.1023 | 4.54 | 31.16 |
| 20.00 | 321.38 | 0.1023 | 4.44 | 17.18 |
| 20.32 | 1871.18 | 0.1279 | 4.37 | 100.00 |
| 20.87 | 440.36 | 0.1279 | 4.26 | 23.53 |
| 21.32 | 222.29 | 0.1023 | 4.17 | 11.88 |
| 21.82 | 540.73 | 0.1279 | 4.07 | 28.90 |
| 22.43 | 627.86 | 0.1279 | 3.96 | 33.55 |
| 22.91 | 723.97 | 0.1279 | 3.88 | 38.69 |
| 23.58 | 933.68 | 0.1791 | 3.77 | 49.90 |
| 24.09 | 855.62 | 0.1279 | 3.69 | 45.73 |
| 24.59 | 884.95 | 0.1279 | 3.62 | 47.29 |
| 24.97 | 565.38 | 0.1279 | 3.57 | 30.22 |
| 25.25 | 304.05 | 0.1279 | 3.53 | 16.25 |
| 25.79 | 1462.26 | 0.1279 | 3.45 | 78.15 |
| 26.33 | 826.02 | 0.1279 | 3.39 | 44.14 |
| 27.01 | 466.74 | 0.1535 | 3.30 | 24.94 |
| 28.30 | 423.47 | 0.1535 | 3.15 | 22.63 |
| 29.24 | 143.19 | 0.2047 | 3.05 | 7.65 |
| 29.99 | 211.10 | 0.3582 | 2.98 | 11.28 |
| 30.62 | 196.94 | 0.1791 | 2.92 | 10.52 |
| 32.09 | 53.11 | 0.3070 | 2.79 | 2.84 |
| 33.53 | 109.79 | 0.1535 | 2.67 | 5.87 |
| 34.63 | 127.16 | 0.2047 | 2.59 | 6.80 |
| 35.38 | 203.67 | 0.1791 | 2.54 | 10.88 |
| 37.94 | 113.41 | 0.2047 | 2.37 | 6.06 |
| 38.58 | 91.48 | 0.2047 | 2.33 | 4.89. |

Figures 11, 12:
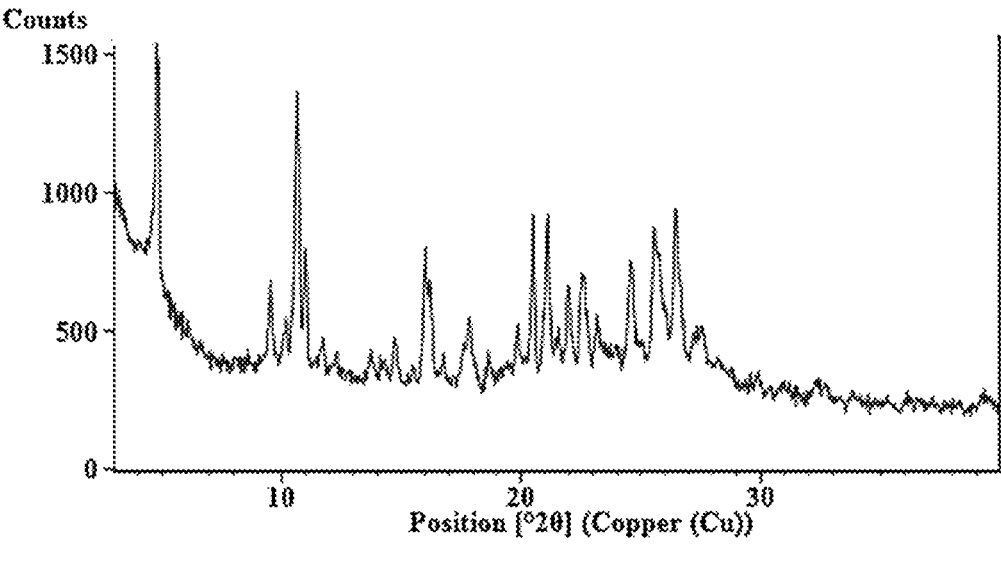
FIG. 11 is XRPD pattern of the crystalline form V of fluvatinib mesylate.
FIG. 12 is XRPD pattern of the crystalline form VI of fluvatinib mesylate.

Example 6 Preparation of the Crystalline Form V of the Fluvatinib Methanesulfonate About 1.0 g of fluvatinib methanesulfonate was weighed and added to a mixed solvent system of 4 mL tetrahydrofuran/4 mL water (1:1), to form a suspension. The suspension sample was stirred using a magnetic stirrer at 20-30° C., become a brown suspension after 48 h, and filtered. The filter cake was dried at 40-50° C. with spinning under reduced pressure, to obtain a dry sample 430 mg with a yield of 43.00%. The sample was detected by XRPD. The results are shown in Table 5 and FIG. 11, indicating that the sample is the crystalline form V of fluvatinib mesylate.

TABLE 5

| | XRPD diffraction data of the crystalline form V of fluvatinib mesylate | | | |
|---|---|---|---|---|
| Pos. [°2θ] | Height [cts] | FWHM Left [°2θ] | d-spacing [Å] | Rel. Int. [%] |
| 4.81 | 889.42 | 0.1279 | 18.36 | 87.69 |
| 9.54 | 312.80 | 0.1023 | 9.27 | 30.84 |

TABLE 5-continued

| | XRPD diffraction data of the crystalline form V of fluvatinib mesylate | | | |
|---|---|---|---|---|
| Pos. [°2θ] | Height [cts] | FWHM Left [°2θ] | d-spacing [Å] | Rel. Int. [%] |
| 10.64 | 1014.28 | 0.1535 | 8.31 | 100.00 |
| 10.99 | 444.45 | 0.1023 | 8.05 | 43.82 |
| 11.69 | 117.55 | 0.1535 | 7.57 | 11.59 |
| 14.74 | 139.06 | 0.1535 | 6.01 | 13.71 |
| 16.00 | 439.50 | 0.1023 | 5.54 | 43.33 |
| 17.83 | 219.37 | 0.1535 | 4.97 | 21.63 |
| 19.85 | 181.41 | 0.1535 | 4.47 | 17.89 |
| 20.50 | 601.68 | 0.1023 | 4.33 | 59.32 |
| 21.10 | 596.03 | 0.1279 | 4.21 | 58.76 |
| 21.97 | 332.97 | 0.1279 | 4.05 | 32.83 |
| 22.57 | 365.58 | 0.2558 | 3.94 | 36.04 |
| 23.18 | 198.16 | 0.2047 | 3.84 | 19.54 |
| 24.59 | 406.40 | 0.2303 | 3.62 | 40.07 |
| 25.57 | 531.76 | 0.1023 | 3.48 | 52.43 |
| 26.46 | 602.59 | 0.1279 | 3.37 | 59.41 |
| 27.44 | 148.11 | 0.4093 | 3.25 | 14.60 |
| 32.46 | 43.13 | 0.6140 | 2.76 | 4.25. |

Example 7 Preparation of the Crystalline Form VI of the Fluvatinib Methanesulfonate About 2.0 g of fluvatinib free base was weighed and added to methanol in a reaction flask to form a suspension, and added with 0.32 mL of methanesulfonic acid while being stirred at 20-30° C. The reaction solution was stirred at 20-30° C. for 4 h, and filtered. The filter cake was dried at 40-50° C. with spinning under reduced pressure, to obtain a dry sample. The sample was detected by XRPD. The results are shown in Table 6 and FIG. 12, indicating that the sample is the crystalline form VI of fluvatinib mesylate (Form VI).

TABLE 6

| | XRPD diffraction data of the crystalline form VI of fluvatinib mesylate | | | |
|---|---|---|---|---|
| Pos. [°2θ] | Height [cts] | FWHM Left [°2θ] | d-spacing [Å] | Rel. Int. [%] |
| 5.61 | 5735.70 | 0.1023 | 15.75 | 100.00 |
| 6.78 | 331.22 | 0.1279 | 13.05 | 5.77 |
| 9.98 | 4786.31 | 0.1279 | 8.86 | 83.45 |
| 10.61 | 2778.82 | 0.1279 | 8.34 | 48.45 |
| 11.18 | 842.59 | 0.1279 | 7.91 | 14.69 |
| 12.85 | 104.45 | 0.2047 | 6.89 | 1.82 |
| 13.51 | 564.63 | 0.1535 | 6.55 | 9.84 |
| 14.84 | 80.33 | 0.3070 | 5.97 | 1.40 |
| 15.58 | 345.24 | 0.1279 | 5.69 | 6.02 |
| 15.83 | 420.20 | 0.1279 | 5.60 | 7.33 |
| 16.84 | 1678.51 | 0.2558 | 5.27 | 29.26 |
| 20.14 | 2420.84 | 0.1535 | 4.41 | 42.21 |
| 20.89 | 1209.62 | 0.2047 | 4.25 | 21.09 |
| 22.04 | 155.45 | 0.2047 | 4.03 | 2.71 |
| 23.53 | 206.63 | 0.2047 | 3.78 | 3.60 |
| 24.80 | 833.72 | 0.1791 | 3.59 | 14.54 |
| 25.62 | 909.32 | 0.1791 | 3.48 | 15.85 |
| 27.56 | 97.82 | 0.3070 | 3.24 | 1.71 |
| 29.24 | 262.55 | 0.2047 | 3.05 | 4.58 |
| 30.18 | 79.27 | 0.3070 | 2.96 | 1.38 |
| 31.24 | 237.67 | 0.2047 | 2.86 | 4.14 |
| 32.04 | 410.66 | 0.2303 | 2.79 | 7.16 |
| 33.90 | 47.10 | 0.6140 | 2.64 | 0.82 |
| 36.95 | 62.03 | 0.3070 | 2.43 | 1.08. |

Figure 13:
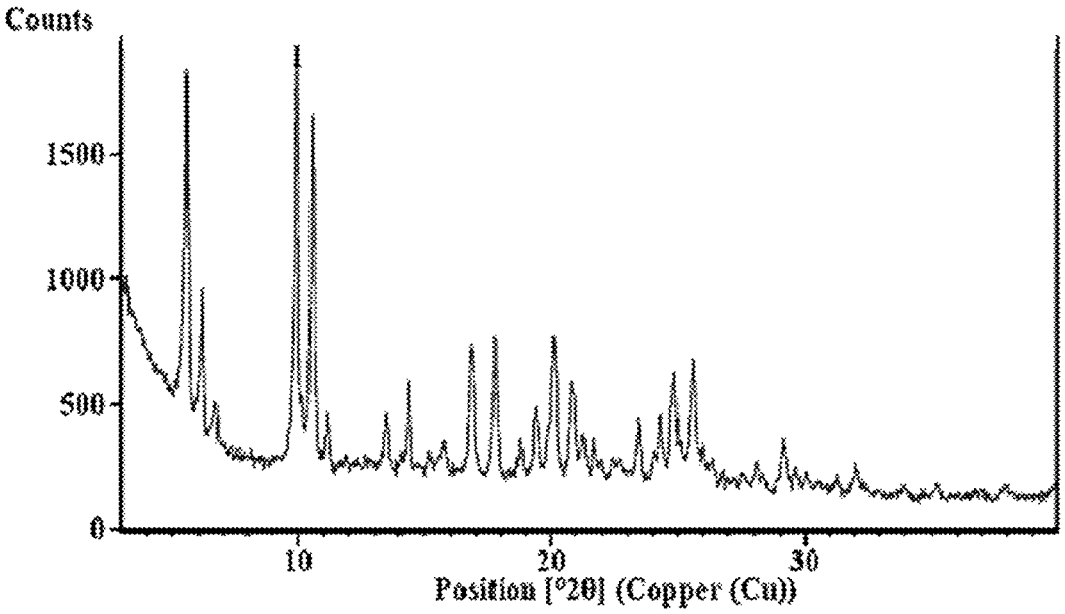
FIG. 13 is XRPD pattern of the crystalline form VII of fluvatinib mesylate.

Example 8 Preparation of the Crystalline Form VII of Fluvatinib Methanesulfonate About 0.2 g of the crystalline form VI of fluvatinib methanesulfonate obtained in Example 7 was weighed and added to ethanol solvent to form a suspension. The suspension was stirred at 20-30° C. using a magnetic stirrer for 4 h, and then filtered. The filter cake was dried at 40-50° C. with spinning under reduced pressure. The obtained dry sample was detected by XRPD. The results are shown in Table 7 and FIG. 13, indicating that the sample is the crystalline form VII of fluvatinib mesylate (Form VII).

TABLE 7

XRPD diffraction data of the crystalline
form VII of fluvatinib mesylate

| Pos. [°2θ] | Height [cts] | FWHM Left [°2θ] | d-spacing [Å] | Rel. Int. [%] |
|---|---|---|---|---|
| 5.57 | 1352.56 | 0.1023 | 15.86 | 80.05 |
| 6.17 | 521.82 | 0.1023 | 14.32 | 30.89 |
| 6.69 | 121.82 | 0.2047 | 13.21 | 7.21 |
| 9.93 | 1689.54 | 0.1023 | 8.91 | 100.00 |
| 10.56 | 1384.01 | 0.1279 | 8.38 | 81.92 |
| 11.15 | 189.94 | 0.1535 | 7.94 | 11.24 |
| 13.47 | 213.05 | 0.1279 | 6.57 | 12.61 |
| 14.34 | 359.10 | 0.1023 | 6.18 | 21.25 |
| 15.68 | 93.94 | 0.3070 | 5.65 | 5.56 |
| 16.81 | 488.60 | 0.1791 | 5.27 | 28.92 |
| 17.76 | 550.01 | 0.1023 | 4.99 | 32.55 |
| 18.77 | 108.72 | 0.2047 | 4.73 | 6.43 |
| 19.37 | 272.68 | 0.1279 | 4.58 | 16.14 |
| 20.10 | 563.56 | 0.1535 | 4.42 | 33.36 |
| 20.81 | 387.35 | 0.1535 | 4.27 | 22.93 |
| 21.26 | 168.67 | 0.1535 | 4.18 | 9.98 |
| 23.46 | 238.07 | 0.1535 | 3.79 | 14.09 |
| 24.29 | 268.93 | 0.1023 | 3.66 | 15.92 |
| 24.85 | 440.06 | 0.2303 | 3.58 | 26.05 |
| 25.60 | 497.89 | 0.1791 | 3.48 | 29.47 |
| 28.10 | 101.35 | 0.1535 | 3.18 | 6.00 |
| 29.16 | 187.94 | 0.2047 | 3.06 | 11.12 |
| 32.07 | 99.98 | 0.2047 | 2.79 | 5.92. |

Example 9 Investigation on Stability of the Crystalline Form I of Fluvatinib

The crystalline form I of fluvatinib was placed in an organic solvent and a water-containing organic solvent, and stirred at 40° C. for 2 days to investigate whether there was a crystal transformation.

Figure 14:
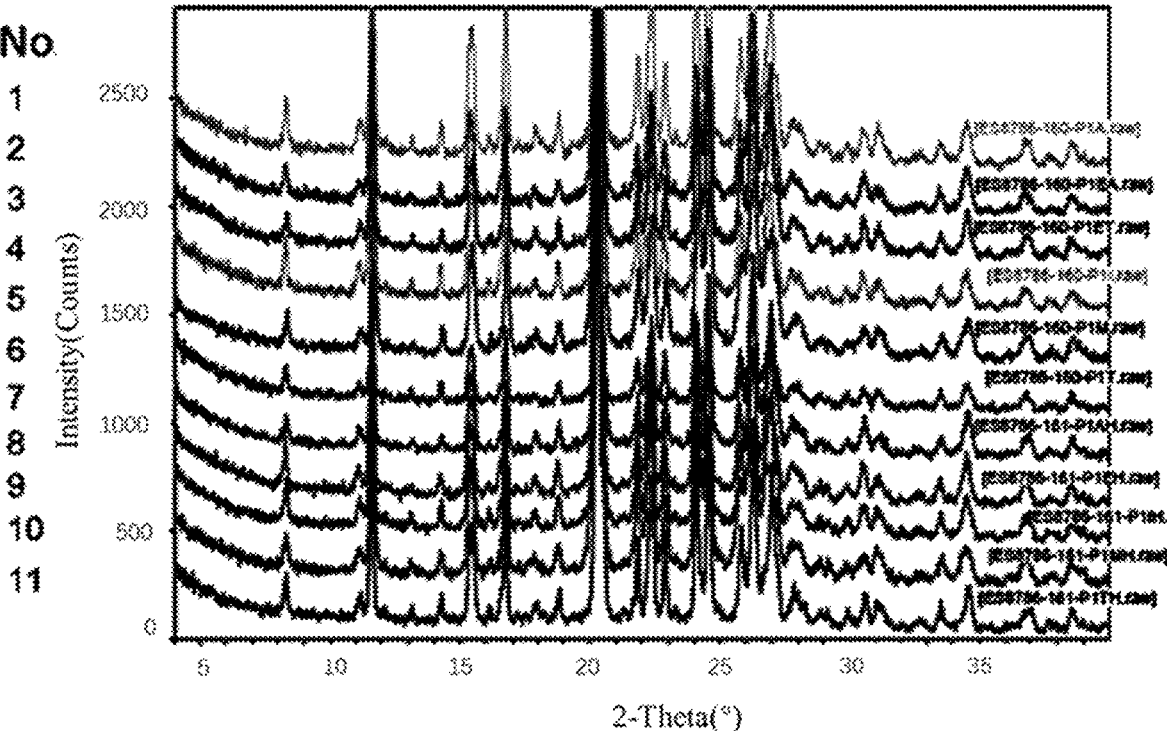
FIG. 14 are XRPD patterns of the crystalline form I of fluvatinib after the crystal transformation test in Example 9.

A number parts of about 30 mg of the crystalline form I of fluvatinib (Form I) were respectively weighed and added to different glass bottles, and added with an appropriate amount of a single organic solvent or a mixture containing water (see Table 8) to form suspensions. The above-mentioned suspension samples were placed on magnetic stirrers (40° C.) to perform a stirring test. After being stirring at 40° C. for 2 days, the suspension samples were filtered. The filter cake samples were then dried overnight in a vacuum dry box (40° C.), and the dried samples were detected by XRPD (see Table 8 and FIG. 14). The results indicates that the crystalline form I of fluvatinib is stable in various solvents (especially in solvents containing water), without occurrence of crystal transformation, which is suitable for the industrial production of its preparations.

TABLE 8

Solvents and crystalline forms after stirring for 2 days

| No. | solvents | amounts of solvents (mL) | state under stirring for 2 days | crystalline form |
|---|---|---|---|---|
| 1 | methanol | 0.4 | suspension | Form I |
| 2 | ethanol | 0.4 | suspension | Form I |
| 3 | ethyl acetate | 0.4 | suspension | Form I |
| 4 | acetone | 0.4 | suspension | Form I |
| 5 | THF | 0.4 | suspension | Form I |
| 6 | isopropanol | 0.4 | suspension | Form I |
| 7 | methanol-water (3:1) | 0.4 | suspension | Form I |
| 8 | ethanol-water (3:1) | 0.4 | suspension | Form I |
| 9 | acetone-water (1:2) | 0.4 | suspension | Form I |
| 10 | isopropanol-water (1:1) | 0.4 | suspension | Form I |
| 11 | THF-water (1:1) | 0.4 | suspension | Form I |

Example 10 Investigation of the Stability of the Crystalline Form I of Fluvatinib Mesylate The crystalline form I of fluvatinib mesylate was stored in acetone, ethanol and ethyl acetate to investigate whether there was a crystal transformation.

3 parts of about 50 mg the crystalline form I of fluvatinib mesylate were weighed and respectively added to reaction flasks containing an appropriate amount of acetone, ethanol, or ethyl acetate solvent. The suspension samples were placed on magnetic stirrers, stirred for 10 h at room temperature, and filtered. The filter cake was dried at 40-50° C. with spinning under reduced pressure. The obtained dry samples were detected by XRPD. The test results shows that its 2θ degrees of XRPD are basically consistent with those in FIG. 4 (within the error range). It can be concluded that the crystalline form I of the fluvatinib methanesulfonate maintained its form in single solvent of ethanol, acetone, or ethyl acetate, indicating that the crystalline form I of fluvatinib mesylate has good stability.

Figure 15:
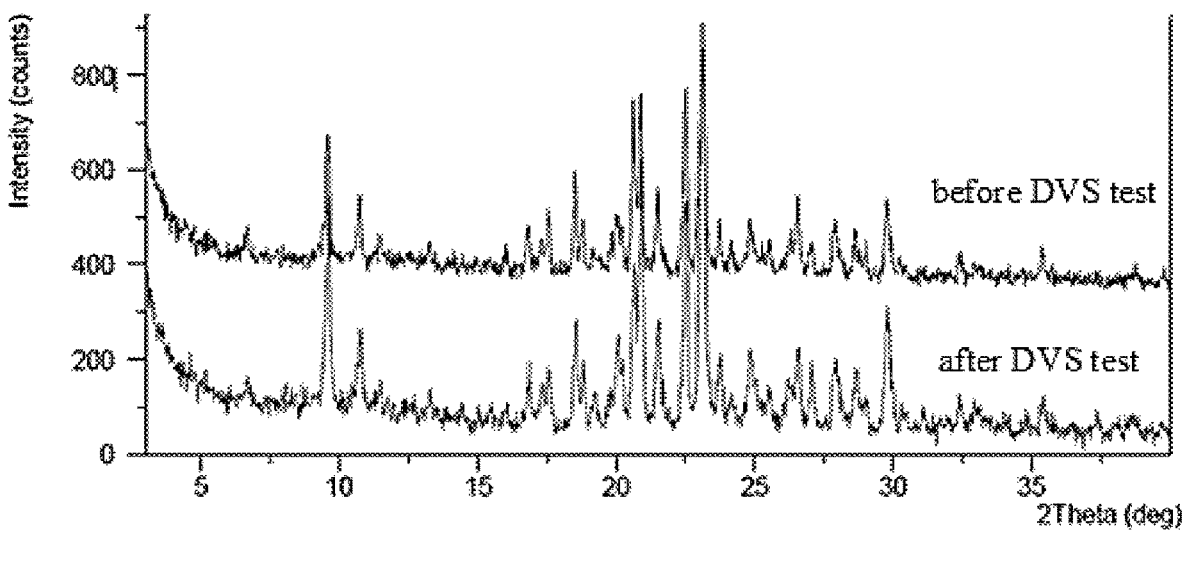
FIG. 15 is XRPD patterns of the crystalline form I of fluvatinib mesylate before and after the DVS test in Example 10.

At the same time, the crystalline form I of fluvatinib mesylate was tested for dynamic hygroscopicity by DVS to detect water content. The results show that the methanesulfonate salt has a hygroscopic weight gain of 1.3% under the condition of 25° C./80% RH, indicating that the sample has slight hygroscopicity, and the crystalline form of the sample did not undergo crystal transformation after DVS measurements (see FIG. 15). This indicates again that the crystalline form I of fluvatinib mesylate has good stability.

Example 11 Investigation on Stability of the Crystalline Form III of Fluvatinib Mesylate 1. Investigation of the Stability of the Crystalline Form III of Fluvatinib Mesylate in Air (Oxygen Gas)

To investigate the stability of the crystalline form III of fluvatinib mesylate (Form III), Form III was exposed to air and contacted with oxygen. The results are shown in Table 9. As can be seen from the results, the methanesulfonate salts can exist stably when exposed to the air at 20-30° C. and 60° C., and the methanesulfonate salts have stable oxdation resistance, without producing extra visible impurities.

TABLE 9

| Stability data of the crystalline form III of fluvatinib mesylate in oxygen gas | | | | |
|---|---|---|---|---|
| | | oxidation | | |
| | crystalline | 20-30° C. | | 60° C. | |
| No. | form | 0 hour | 24 hours | 0 hour | 24 hours |
| 1 | Form III | 93.66% | 94.10% | 93.61% | 94.00% |

2. Investigation of the Crystal Transformation in Organic Solvents

The crystalline form of the fluvatinib methanesulfonate was investigated on its stability in ethanol, to see whether there is crystal transformation.

Figure 16:
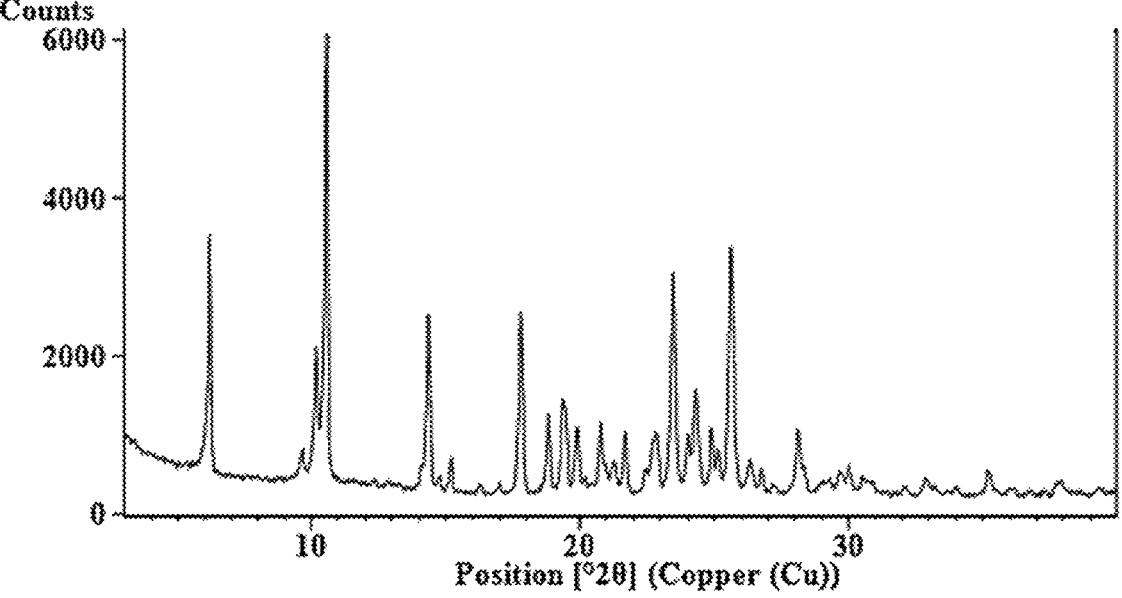
FIG. 16 is XRPD pattern of the crystalline form III of fluvatinib mesylate obtained from the crystal transformation experiment in Example 11.

About 0.15 g of the crystalline forms II (Form II), III (Form III), VI (Form VI) and VII (Form VII) of the fluvatinib mesylate were weighed and respectively added to reaction flasks containing ethanol, stirred magnetically for 2 days at room temperature, and filtered. The filter cakes were dried at 40-50° C. with spinning under reduced pressure. The obtained dried samples were detected by XRPD. The results showed that all samples were Form III, indicating that Form III did not undergo crystal transformation, whereas Form II, Form VI and Form VII undergone crystal transformation and converted to Form III as shown in FIG. 16. This indicates that the crystalline form III of fluvatinib mesylate has good stability, and is suitable and adaptable to the processing process of preparations, particularly for preparing tablets or granules of fluvatinib methanesulfonate by the granulation and tableting process containing ethanol as a binder or wetting agent.

Figure 17:
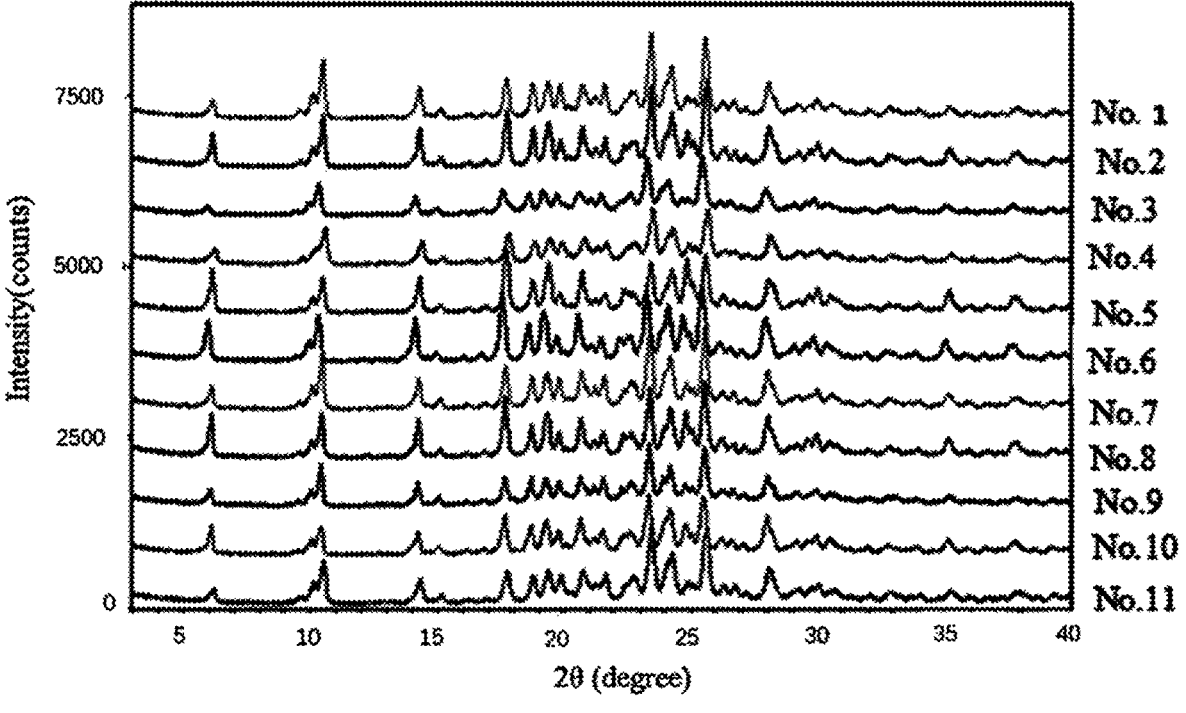
FIG. 17 are XRPD patterns of the crystalline form in high temperature suspension experiment in Example 11.

3. Investigation of the Stability of the Crystalline Form III of Fluvatinib Mesylate in Various Organic Solvents The crystalline form III of fluvatinib mesylate was subjected to high temperature suspension experiments (50° C.), to investigate whether the crystalline form III of fluvatinib mesylate undergoes crystal transformation in various type of common organic solvents, and whether it is stable. The crystalline form III of fluvatinib mesylate was suspended in 12 types of organic solvents (in 1 mL of solvent) and water as set forth in Table 10 at a temperature of 50° C. and an amount of about 25 mg for 24 hours. The experiment conditions and results are shown in Table 10. The solids after being suspended in the organic solvents were detected by XRPD. The results shows that they all have the 2θ characteristic peaks of the crystal form III (see FIG. 17).

TABLE 10

| High temperature suspension experiment and results | | | | |
|---|---|---|---|---|
| solvent No. | solvent | solid weight (mg) | solution volume (mL) | XRD results |
| 1 | ethanol | 25 | 1 | Form III |
| 2 | isopropanol | 25 | 1 | Form III |
| 3 | acetone | 25 | 1 | Form III |
| 4 | cyclohexane | 25 | 1 | Form III |
| 5 | acetonitrile | 25 | 1 | Form III |
| 6 | tetrahydrofuran | 25 | 1 | Form III |
| 7 | ethyl acetate | 25 | 1 | Form III |
| 8 | n-hexane | 25 | 1 | Form III |

TABLE 10-continued

| High temperature suspension experiment and results | | | | |
|---|---|---|---|---|
| solvent No. | solvent | solid weight (mg) | solution volume (mL) | XRD results |
| 9 | n-heptane | 25 | 1 | Form III |
| 10 | 1.4-dioxane | 25 | 1 | Form III |
| 11 | dichloromethane | 25 | 1 | Form III |

Example 12 Investigation on the Hydrothermal Stability of the Crystalline Forms of Fluvatinib Mesylate The crystalline forms I, III, IV, V, VI, and VII of fluvatinib mesylate of the present disclosure were placed in harsh environments to investigate their stability. They were placed under high temperature and high humidity conditions: 25° C. 92.5% R.H for 7 days, 40° C. 75% R.H for 14 days, and 60° C. for 14 days, and then detected by XRPD. The results are shown in Table 11.

TABLE 11

| Experimental results of the hydrothermal stability of the crystalline forms of fluvatinib mesylate | | | | |
|---|---|---|---|---|
| crystalline form | lot number | 25° C. 92.5% R.H for 7 days | 40° C. 75% R.H for 14 days | 60° C. for 14 days |
| I | P-JZ-200303-CYM | no crystal transformation | no crystal transformation | no crystal transformation |
| III | P-200228-CYM | no crystal transformation | no crystal transformation | no crystal transformation |
| V | P-200418-XPY-2 | converted to crystalline form III | converted to crystalline form III | converted to crystalline form III |
| VI | P-200422-XPY-1 | converted to crystalline form III | converted to crystalline form III | converted to crystalline form III |
| VII | P-200422-XPY-2 | converted to crystalline form III | converted to crystalline form III | converted to crystalline form III |

The results in Table 11 show that the crystalline form I and crystalline form III of fluvatinib mesylate did not undergo crystal transformation under high temperature and high humidity conditions, exhibiting good stability. Whereas the crystalline forms V, VI, VII of fluvatinib mesylate undergone crystal transformation under high temperature and high humidity conditions, exhibiting instability to high temperature and high humidity.

Example 13 Hygroscopicity Investigation

The crystalline form III of fluvatinib mesylate was tested for hygroscopicity under humidity conditions of 25° C., 0-90% RH, using a dynamic moisture tester a dynamic vapor sorption (DVS) analyzer. The results are shown in FIG. 18.

Figure 18:
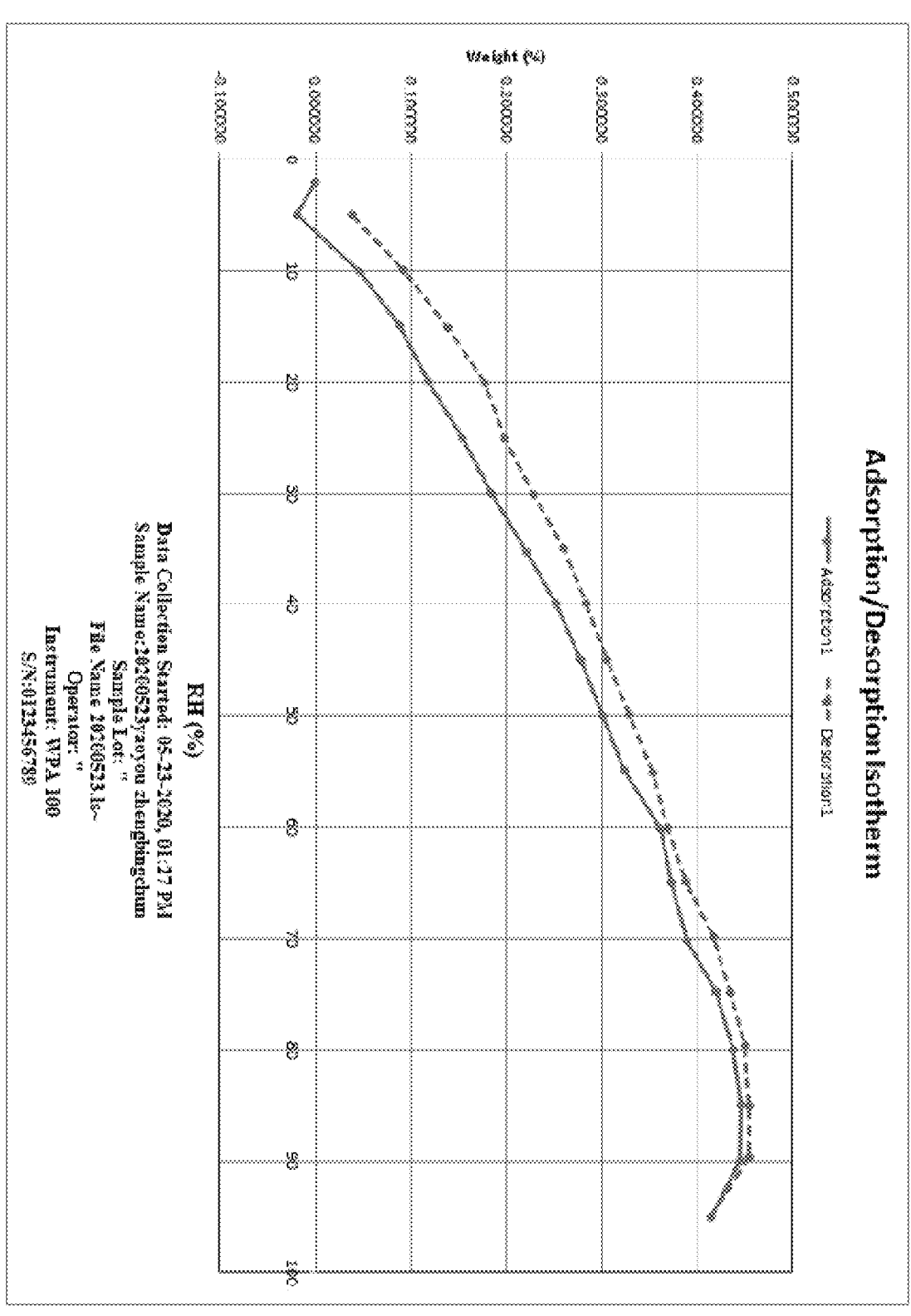
FIG. 18 are DVS curves of the crystalline form III of fluvatinib mesylate.

The results in FIG. 18 show that the crystalline form III of fluvatinib mesylate has a hygroscopic weight of 0.44%, exhibiting low hygroscopicity and thus stability to moisture.

Example 14 Formulation

| formulation parts | percentages by weight |
|---|---|
| crystalline form I or III of fluvatinib mesylate | 30% |
| anhydrous lactose | 45% |
| direct compression starch | 23% |
| magnesium stearate | 2% |

The formula amounts of the crystalline form of fluvatinib mesylate, anhydrous lactose and direct compression starch were mixed, and then mixed with magnesium stearate. The mixture was prepared into tablets by direct compression method, with each table weighed 200 mg.

Figure 19:
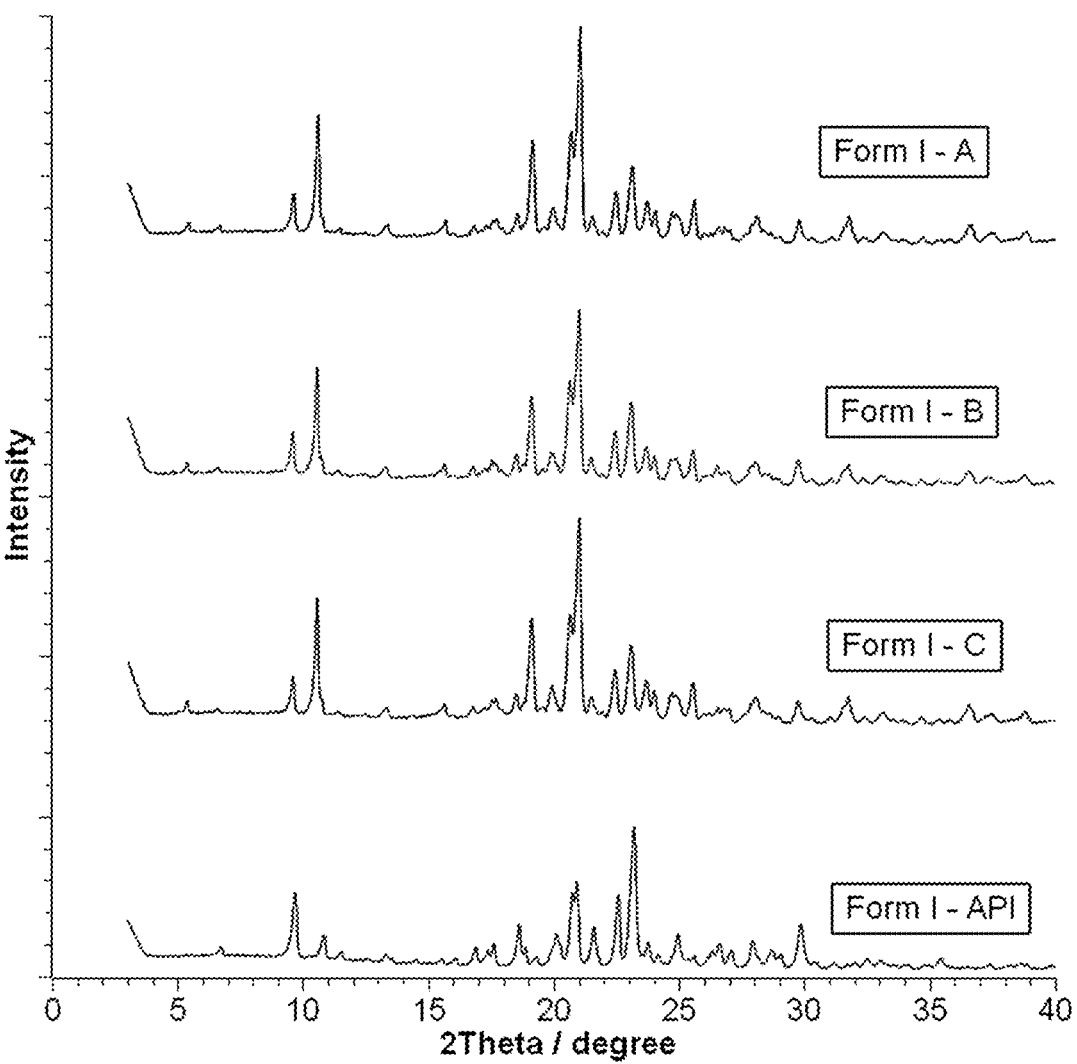
FIG. 19 are XRPD patterns of the crystalline form I of fluvatinib mesylate before and after tableting, and having been placed for 6 months.
Figure 20:
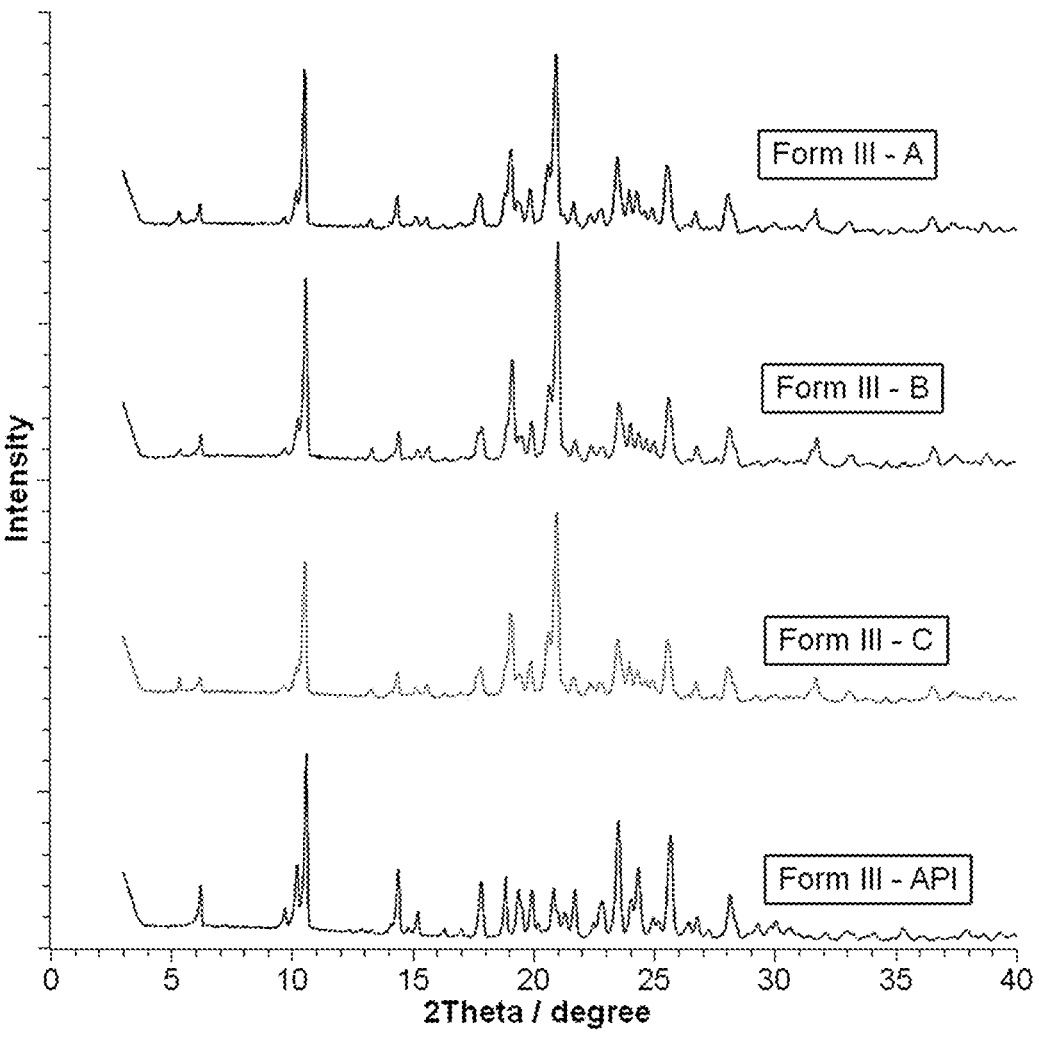
FIG. 20 are XRPD patterns of the crystalline form III of fluvatinib mesylate before and after tableting, and having been placed for 6 months.

The crystalline forms before and after being prepared into tablets and after the tablets being placed in 40° C., 75% RH environment for 6 months were detected by XRPD. The results are shown in FIGS. 19 and 20, wherein A, B, and C represent XRPD patterns of the crystalline form before and after being prepared into tablets and after the tablets being placed for 6 months. The XRPD pattern comparison between the test sample and crystalline forms of the active pharmaceutical ingredients (API), shows that neither the crystalline form I of fluvatinib mesylate nor the crystalline form III of fluvatinib mesylate undergoes crystal transformation during the process of preparing tablets, and no crystal transformation occurred after the tablets being placed for 6 months.

The above test results show that the crystalline forms I and III of fluvatinib mesylate remain stable in the formulation processing, and exhibit good stability in high temperature and high humidity environments, indicating excellent stability of crystalline forms I and III.

The invention claimed is:

1. A crystalline form III of fluvatinib mesylate, wherein the fluvatinib mesylate is represented by the following chemical formula:

$\cdot CH_3SO_3H$ and its X-ray powder diffraction pattern has characteristic diffraction peaks at 2θ degrees of 6.28±0.2°, 10.25±0.2°, 10.65±0.2°, 14.44±0.2°, 15.28±0.2°, 17.87±0.2°, 18.91±0.2°, 19.48±0.2°, 19.98±0.2°, 20.86±0.2°, 21.77±0.2°, 22.78±0.2°, 23.57±0.2°, 24.38±0.2° and 24.98±0.2°.

2. A method of preparing the crystalline form III of fluvatinib mesylate according to claim 1, comprising obtaining a mixed solution of fluvatinib mesylate with ethanol, stirring the mixed solution at a temperature of 20-30° C. for 16-48 h or at a temperature of 40° C. for 2-3 h or at a temperature of 55-65° C. for 2-3 h, filtering to obtain a solid, and drying the solid to obtain the crystalline form III of fluvatinib mesylate.

3. A pharmaceutical composition, comprising the crystalline form III of fluvatinib mesylate according to claim 1 and a pharmaceutically acceptable adjuvant.

4. A method of treating a tumor, comprising administering the composition according to claim 3 to a subject in need thereof.

* * * * *